United States Patent
Taishi et al.

(10) Patent No.: US 9,594,017 B2
(45) Date of Patent: Mar. 14, 2017

(54) REFLECTIVE SENSOR

(71) Applicant: OMRON Corporation, Kyoto-shi, Kyoto (JP)

(72) Inventors: Yoshitaka Taishi, Shiga (JP); Hajime Kawai, Kyoto (JP); Hiroyuki Miyamoto, Shiga (JP)

(73) Assignee: OMRON Corporation, Kyoto (JP)

( * ) Notice: Subject to any disclaimer, the term of this patent is extended or adjusted under 35 U.S.C. 154(b) by 0 days.

(21) Appl. No.: 14/831,969

(22) Filed: Aug. 21, 2015

(65) Prior Publication Data
US 2016/0069800 A1 Mar. 10, 2016

(30) Foreign Application Priority Data
Sep. 5, 2014 (JP) .................................. 2014-181686

(51) Int. Cl.
*G03G 15/00* (2006.01)
*G01N 21/00* (2006.01)
(Continued)

(52) U.S. Cl.
CPC ......... *G01N 21/4738* (2013.01); *G01N 21/55* (2013.01); *G01N 21/86* (2013.01);
(Continued)

(58) Field of Classification Search
CPC .......... G03G 15/5058; G03G 15/0855; G03G 15/5041; G03G 15/5062;
(Continued)

(56) References Cited

U.S. PATENT DOCUMENTS 4,553,033 A * 11/1985 Hubble, III ............ G01N 21/55
  250/341.8
5,438,187 A * 8/1995 Reddersen ......... G06K 7/10811
  235/462.22
(Continued)

FOREIGN PATENT DOCUMENTS

EP   1 657 598 A1   5/2006
EP   1 988 428 A2   11/2008
(Continued)

OTHER PUBLICATIONS

Extended European Search Report in counterpart European Application No. 15 18 1498.5 issued Jan. 29, 2016 (9 pages).

*Primary Examiner* — Robert Beatty
(74) *Attorney, Agent, or Firm* — Osha Liang LLP

(57) ABSTRACT

The present invention includes an optical system disposed on an optical path of light that is emitted by a light emitting section, travels to a detection target object, is reflected by the detection target object, and reaches a light receiving section. The optical system, in a sub scanning direction, that is, the direction in which a detection target object is moving, collects light so that the light receiving section has, for light from the light emitting section, a regularly reflected light receiving area and a diffuse-reflected light receiving area that differ from each other in position within a predetermined range. The optical system, in a perpendicular direction that is perpendicular to the movement direction, refracts light so that a light receiving area, which covers the regularly reflected light receiving area and the diffuse-reflected light receiving area, is wider in the perpendicular direction than in the sub scanning direction.

12 Claims, 20 Drawing Sheets

(51) Int. Cl.
*G01N 21/47* (2006.01)
*G01N 21/55* (2014.01)
*G01N 21/86* (2006.01)

(52) U.S. Cl.
CPC ..... *G03G 15/5041* (2013.01); *G03G 15/5058* (2013.01); *G03G 2215/00042* (2013.01); *G03G 2215/00059* (2013.01); *G03G 2215/0161* (2013.01)

(58) Field of Classification Search
CPC . G03G 2215/00059; G03G 2215/0161; G03G 2215/00042; G03G 2215/00063; G03G 2215/00067; G03G 2215/00616; G03G 2215/00755; G01N 21/86; G01N 21/55; G01N 21/4738
USPC .......................................... 399/49, 60, 64, 74
See application file for complete search history.

(56) References Cited

U.S. PATENT DOCUMENTS

| | | | |
|---|---|---|---|
| 5,768,471 A * | 6/1998 | Meredith, Jr. ......... | G01N 21/89 356/445 |
| 6,462,821 B1 | 10/2002 | Borton et al. | |
| 7,655,936 B2 * | 2/2010 | Sawayama ............. | G01N 21/55 250/559.4 |
| 8,913,096 B2 * | 12/2014 | Sakai ...................... | B41J 2/473 347/130 |
| 9,116,130 B2 * | 8/2015 | Suzuki ............... | G01N 21/8903 356/237.2 |
| 2002/0051648 A1 * | 5/2002 | Shimomura ......... | H04N 1/0473 399/49 |
| 2003/0112486 A1 * | 6/2003 | Kudo ................... | G02B 26/123 359/216.1 |
| 2007/0253048 A1 * | 11/2007 | Sakai ................... | G02B 26/124 359/204.5 |
| 2009/0238585 A1 * | 9/2009 | Hayashi ............. | G03G 15/0194 399/40 |
| 2010/0266302 A1 | 10/2010 | Suzuki et al. | |
| 2012/0237246 A1 | 9/2012 | Taishi et al. | |
| 2013/0094875 A1 | 4/2013 | Ogata et al. | |
| 2014/0071443 A1 | 3/2014 | Suzuki et al. | |

FOREIGN PATENT DOCUMENTS

| | | | |
|---|---|---|---|
| JP | 07214761 A | * | 8/1995 |
| JP | 4717189 B2 | | 7/2011 |
| JP | 5327302 B2 | | 10/2013 |

* cited by examiner (Sub scanning direction)

(Main scanning direction)

Case of symmetrical aspheric lens (For reference)

Case of anamorphic lens (Conventional example)

REFLECTIVE SENSOR

This Nonprovisional application claims priority under 35 U.S.C. §119 on Patent Application No. 2014-181686 filed in Japan on Sep. 5, 2014, the entire contents of which are hereby incorporated by reference.

TECHNICAL FIELD

The present invention relates to a reflective sensor for detecting reflected light from a moving detection target object.

BACKGROUND ART

An image forming apparatus such as a copying machine, a printer, or a facsimile machine includes, for example, (i) a toner density sensor for reading the toner density and (ii) a mispositioning sensor for reading the position of an image to detect mispositioning. Such a toner density sensor and mispositioning sensor are each typically a reflective sensor including a light emitting element and a light receiving element.

A reflective sensor is arranged such that a light emitting element irradiates a detection target object with light and that a light receiving element reads reflected light from that detection target object. The light receiving element generates a photocurrent corresponding to the intensity of light that the light receiving element has read. The reflective sensor detects such a photocurrent in terms of a voltage value. The image forming apparatus then forms a toner image of the detection target object on a recording medium or an intermediate transfer member. This allows a reflective sensor to, on the basis of a photocurrent generated (voltage detected), detect the toner density or detect the position of a toner image to detect mispositioning.

Conventional techniques detect toner densities in different manners for different colors having respective characteristics in terms of light absorption and light diffusion. Specifically, conventional techniques detect (i) the density of a black toner on the basis of a voltage detected as a result of reading regularly reflected light and (ii) the density of any color toner such as a cyan toner, a magenta toner, or a yellow toner on the basis of a voltage detected as a result of reading diffuse-reflected light. Conventional techniques detect mispositioning on the basis of either (i) a decrease in the amount of regularly reflected light received or (ii) an increase in the amount of diffuse-reflected light received.

Patent Literature 1, for example, discloses an image forming apparatus including an image detecting device capable of detecting information on the position of an image highly accurately. This image forming apparatus includes (i) a lighting lens for directing light from a light source onto an image on a recording material being carried and (ii) an imaging lens for forming that image on a light receiving element. The image detecting device uses the two lenses to narrow the imaging spot on the light receiving element for minimum spherical aberration in order to detect information on the position of an image highly accurately.

Patent Literature 2 discloses a technique of detecting the amount of mispositioning of an image with use of a reflective sensor for receiving regularly reflected light. This technique uses (i) a first aperture for narrowing light from a lighting source section which light is directed onto a toner image on an image holding member being carried and (ii) a second aperture for narrowing reflected light regularly reflected by the toner image and then received by a light receiving section. The technique sets an optimal diameter for each of the first and second apertures for a balance between robustness and influence of diffused light.

CITATION LIST

Patent Literature 1
Japanese Patent No. 4717189
Patent Literature 2
Japanese Patent No. 5327302

SUMMARY OF INVENTION

Technical Problem

Unfortunately, no conventional technique as described above provides a reflective sensor having not only high accuracy in detecting the position of a detection target object, but also high robustness against a change in (i) the distance between the detection target object and a reference position and (ii) the angle of the detection target object. Thus, in a case where, for instance, a single sensor is used to detect both toner densities (which requires robustness) and mispositioning (which requires accuracy in position detection), such a sensor is problematic in that it is incapable of accurately detecting toner densities and mispositioning at the same time. This problem is discussed below in detail.

The technique of Patent Literature 1 narrows the imaging spot on a light receiving element for increased accuracy in detecting the position of an image. Thus, even a slight change in the distance between a detection target object and the sensor results in a large decrease in the amount of light received. The sensor of Patent Literature 1, as a result, has low robustness against a change in the distance between a detection target object and the sensor. Since detecting a toner density requires reading a plurality of toner images (patches) each having a density gradation, a reflective sensor having low robustness against a change in the distance between a detection target object and the sensor will suffer from decreased accuracy.

The description below deals with how robustness and position detection accuracy are related to each other. FIG. 21 shows explanatory graphs illustrating the relationship between robustness and position detection accuracy of a conventional reflective sensor. (a) of FIG. 21 illustrates a case of a reflective sensor having only a small output (voltage) change in response to (i) a change in the distance between a detection target object and a reference position and (ii) a change in the angle of the detection target object (that is, a reflective sensor having high robustness). Such a reflective sensor outputs a voltage whose waveform has overshoots and undershoots over the distance of a movement of a patch (toner image) (that is, such a reflective sensor has low accuracy in position detection). (b) of FIG. 21 illustrates a case of a reflective sensor having a large output change in response to (i) a change in the distance between a detection target object and the sensor and (ii) a change in the angle of the detection target object with respect to the sensor (that is, a reflective sensor having low robustness). Such a reflective sensor outputs a voltage whose waveform has no overshoots or undershoots over the distance of a movement of a patch (that is, such a reflective sensor has high accuracy in position detection). An output voltage may have a waveform with overshoots and undershoots due to an influence of diffused light (diffuse-reflected light). Decreasing robustness increases accuracy in position detection, whereas increasing robustness decreases accuracy in position detection: There is a trade-off between robustness and accuracy in position detection.

In actual use, a reflective sensor requires robustness against, for example, (i) a distance change and (ii) an angle change with respect to the direction in which the detection target object is moving, the distance change involving a larger change for the detection target object. Detecting a toner density, as described above, requires reading a plurality of toner images (patches) each having a density gradation. An output change due to a distance change or an angle change with respect to a movement direction prevents detection of, for example, a subtle density difference.

The technique of Patent Literature 2 serves to present a point of compromise at which a balance can be attained between robustness and an influence of diffused light (between which there is a trade-off) to reduce the decrease in detection accuracy. However, since this technique is not arranged to actively improve robustness, keeping robustness requires a sacrifice of a portion of diffused light, which sacrifice results in a decrease in the position detection accuracy. Thus, this technique can merely achieve a medium level of accuracy in detecting a toner density or accuracy in detecting mispositioning. Further, the technique of Patent Literature 2 problematically involves no lens and thus merely achieves low efficiency in use of light from a light source section.

The present invention has been made in view of the above problem. It is an object of the present invention to provide a reflective sensor having not only accuracy in detecting the position of a detection target object, but also high robustness against at least (i) a change in the distance between the detection target object and the reflective sensor and (ii) a change in the angle of the detection target object with respect to the direction in which the detection target object is moving.

Solution to Problem

In order to attain the object, a reflective sensor of the present invention includes: a light emitting section for emitting light toward a detection target object moving in a single direction; and a light receiving section for receiving regular reflection of the light, the reflective sensor further comprising: an optical system including at least one lens section each including at least one lens which at least one lens section is disposed on an optical path of light that (i) is emitted by the light emitting section, (ii) travels to the detection target object, (iii) is reflected by the detection target object, and (iv) reaches the light receiving section, the optical system being arranged to, in a movement direction in which the detection target object is moving, collect light so that a regularly reflected light receiving area differs in position from a diffuse-reflected light receiving area by an amount within a predetermined range, the regularly reflected light receiving area being an area present between (i) the detection target object and (ii) the light emitting section and the light receiving section within which area the light emitted by the light emitting section is regularly reflected by the detection target object and is then received by the light receiving section, the diffuse-reflected light receiving area being an area present between (i) the detection target object and (ii) the light emitting section and the light receiving section within which area the light emitted by the light emitting section is diffuse-reflected by the detection target object and is then received by the light receiving section, the optical system being further arranged to, in a perpendicular direction that is perpendicular to the movement direction, refract light so that a light receiving area, which covers the regularly reflected light receiving area and the diffuse-reflected light receiving area, is wider in the perpendicular direction than in the movement direction.

Advantageous Effects of Invention

The present invention achieves an advantage of providing a reflective sensor having not only accuracy in detecting the position of a detection target object, but also robustness higher than conventional against at least (i) a change in the distance between the detection target object and the reflective sensor and (ii) a change in the angle of the detection target object with respect to the direction in which the detection target object is moving.

DESCRIPTION OF EMBODIMENTS

Figure 1:
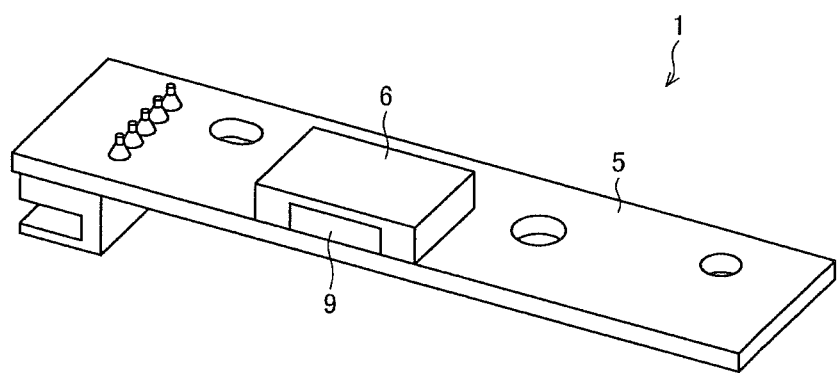
FIG. 1 is a diagram illustrating an appearance of a reflective sensor of an embodiment of the present invention.
Figure 2:
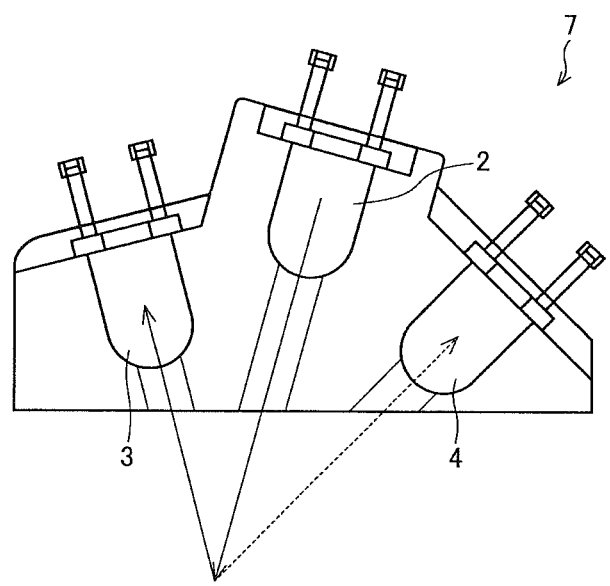
FIG. 2 is a diagram schematically illustrating a configuration of the reflective sensor.
Figure 3:
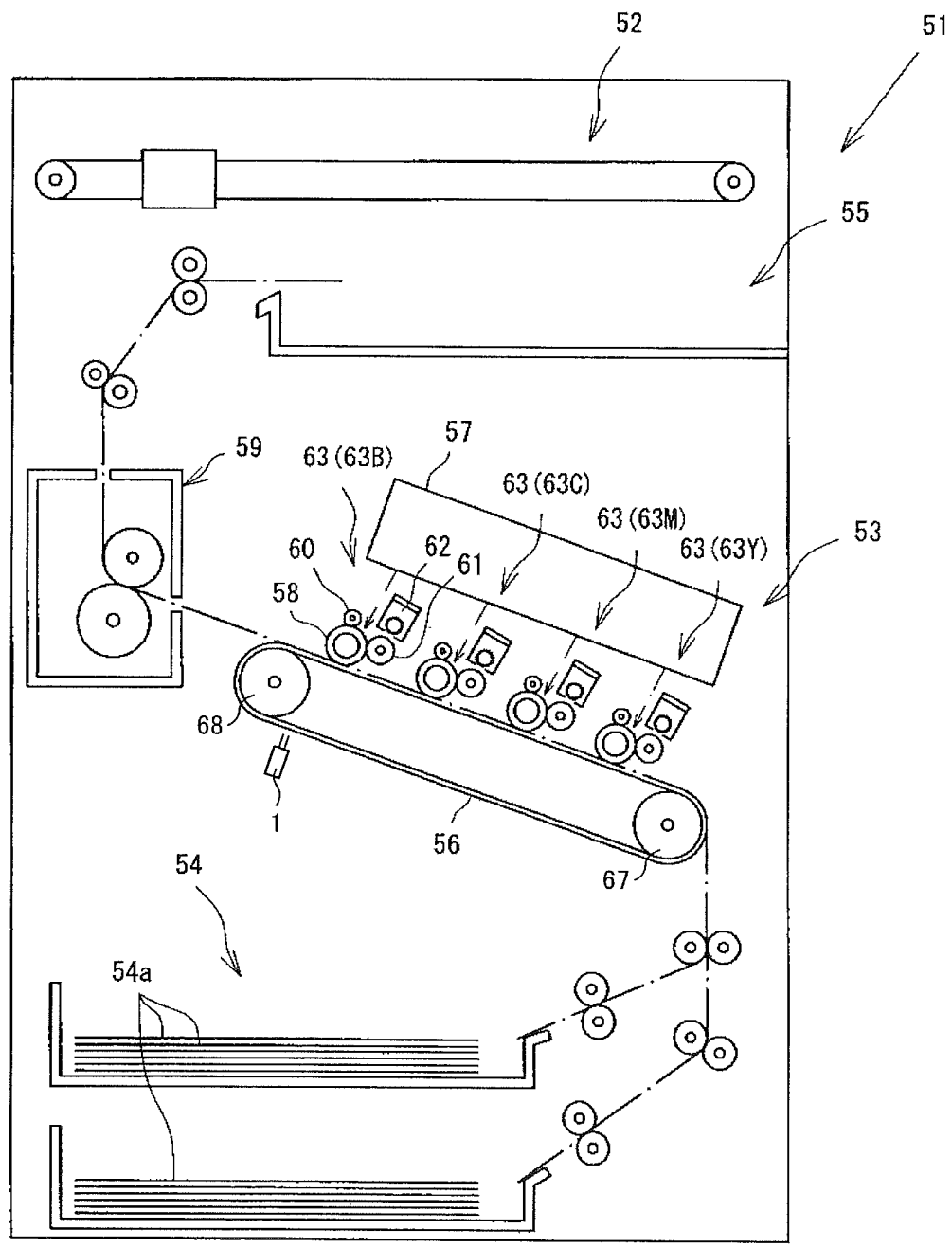
FIG. 3 is a diagram schematically illustrating a configuration of an image forming apparatus including the reflective sensor.
Figure 4:
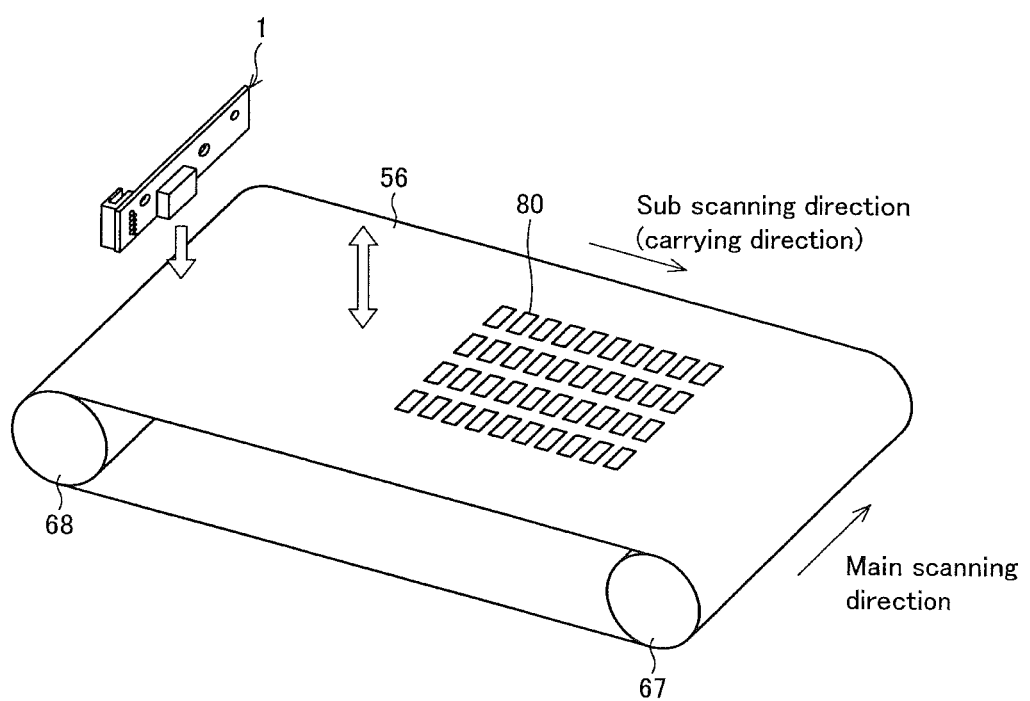
FIG. 4 is a diagram illustrating how the reflective sensor reads a toner patch on a transfer belt.

An embodiment of the present invention is described below in detail. FIG. 1 is a diagram illustrating an appearance of a reflective sensor 1 of the present embodiment. FIG. 2 is a diagram schematically illustrating a configuration of the reflective sensor 1. FIG. 3 is a diagram schematically illustrating a configuration of an image forming apparatus 51 including the reflective sensor 1. FIG. 4 is a diagram illustrating how the reflective sensor reads toner patches (color material images) 80 on a transfer belt 56.

The reflective sensor 1 is mounted in an image forming apparatus such as the image forming apparatus 51 illustrated in FIG. 3. The image forming apparatus 51 is, for example, a color laser printer. The description below first deals with a main structure of the image forming apparatus 51.

The image forming apparatus 51 includes (i) at an upper portion thereof, a document scanning section 52 for scanning a document to prepare document data, (ii) an image creating section 53 for forming an image on the basis of the document data, (iii) at an lower portion of the image forming apparatus 51, a paper feeding section 54 for feeding a sheet 54a onto which the image is transferred, and (iv) at an upper portion of the image forming apparatus 51, a paper output section 55 for outputting the sheet 54a. The image creating section 53 includes a pair of rollers 67 and 68 and a transfer belt 56 provided around the rollers 67 and 68 in a tensioned state. The image creating section 53 further includes an optical writing device 57 for outputting exposure light to photoreceptor drums 58, to which toner (color material) adheres. The image creating section 53 transfers the toner onto the transfer belt 56 (first transfer) to form the image on the transfer belt 56. The paper feeding section 54 then feeds a sheet 54a to the image creating section 53 so that the image on the transfer belt 56 is transferred onto the sheet 54a (second transfer). The sheet 54a is then carried to a fixing section 59, which fixes the toner to the sheet 54a by means of heat and pressure.

FIG. 3 shows the reference numeral "60" to indicate a charging roll, "61" to indicate a development sleeve, and "62" to indicate a toner container. These three members and a photoreceptor drum 58 constitute an image creating unit 63. The image creating section 53 includes four image creating units, namely an image creating unit 63Y for yellow, an image creating unit 63M for magenta, an image creating unit 63C for cyan, and an image creating unit 63B for black.

The reflective sensor 1 is, as illustrated in FIG. 4, so disposed as to face the transfer belt 56 of an image forming apparatus such as the image forming apparatus 51 described above. The reflective sensor 1 detects (i) the density (toner density, color material density) of each toner patch (color material image) 80 on the transfer belt 56 and (ii) mispositioning. Note that FIG. 4 illustrates the transfer belt 56 upside down. The description below uses (i) the term "sub scanning direction" to refer to the direction in which the transfer belt 56 moves (carrying direction) and (ii) the term "main scanning direction" to refer to the direction orthogonal to the direction in which the transfer belt 56 moves. The main scanning direction is a direction in which the optical writing device 57 optically writes an image on a surface of the transfer belt 56.

The description below deals with the reflective sensor 1. The reflective sensor 1, as illustrated in FIG. 2, includes (i) a light emitting element 2 for emitting light to serve as a light emitting section, (ii) light receiving elements 3 and 4 each for receiving reflected light that has been emitted by the light emitting element 2 and then reflected by the transfer belt 56 (see FIG. 3), the light receiving elements 3 and 4 each serving as a light receiving section, and (iii) an amplifier circuit (not shown) for amplifying a voltage generated by each of the light receiving elements 3 and 4 in response to detection of reflected light. The light emitting element 2 includes a light emitting diode, whereas the light receiving elements 3 and 4 each include, for example, a phototransistor or a photodiode.

The light emitting element 2 and the light receiving elements 3 and 4 are, as illustrated in FIG. 1, mounted on a printed circuit board 5. The printed circuit board 5 is provided with a case 6 covering a portion on which the light emitting element 2 and the light receiving elements 3 and 4 are mounted. The case 6 has a light entry/exit surface 9 at a portion along an edge of the printed circuit board 5.

The reflective sensor 1 is arranged as follows: As illustrated in FIG. 2, the light emitting element 2 and the two light receiving elements 3 and 4 are arranged substantially in a straight line. One of the two light receiving elements 3 and 4 (that is, the one on the left in FIG. 2) serves as a first light receiving element 3, which receives a regularly reflected portion of reflected light that has been emitted by the light emitting element 2 and then reflected by the transfer belt 56. The first light receiving element 3 mainly detects (i) the density of a black toner and (ii) mispositioning of a toner image. The other of the two light receiving elements 3 and 4 (that is, the one on the right in FIG. 2) serves as a second light receiving element 4, which receives a diffuse-reflected portion of light that has been emitted by the light emitting element 2 and then reflected by the transfer belt 56. The second light receiving element 4 mainly detects the respective densities of the color toners of yellow, magenta, and cyan.

The reflective sensor 1, in order to accurately detect both (i) the density of a black toner mispositioning of a toner image, includes an optical system A including a lens section including at least one lens, the optical system A being disposed on an optical path of light that is emitted by the light emitting element (light emitting section) 2 to strike a surface of the transfer belt 56 (detection target object) and that is then reflected by the transfer belt 56 to reach the first light receiving element (light receiving section) 3. The description below uses the term "regularly reflected light receiving area" (that is, an area within which to receive a regularly reflected portion of light emitted by the light emitting element 2) to refer to an area present between (i) a detection target object and (ii) the light emitting section and the light receiving section within which area the light emitted by the light emitting element 2 is regularly reflected by the detection target object and is then received by the first light receiving element 3. The description below further uses the term "diffuse-reflected light receiving area" (that is, an area within which to receive a diffuse-reflected portion of light emitted by the light emitting element 2) to refer to an area present between (i) a detection target object and (ii) the light emitting section and the light receiving section within which area the light emitted by the light emitting element 2 is diffuse-reflected by the detection target object and is then received by the first light receiving element 3. The optical system A is arranged to (i) with respect to the sub scanning direction (that is, the direction in which the transfer belt 56 moves), collect light so that the positional difference is smaller between the regularly reflected light receiving area and diffuse-reflected light receiving area on the first light receiving element (light receiving section) 3 and (ii) with respect to the main scanning object (that is, the direction orthogonal to the direction in which the transfer belt 56 moves), refract light to allow the first light receiving element 3 to have a light receiving area (including the regularly reflected light receiving area and the diffuse-reflected light receiving area) that is wider in the main scanning direction than in the sub scanning direction.

The term "predetermined range" is a range set as appropriate so that the reflective sensor 1 is capable of detecting the position of a detection target object with an accuracy that falls within a desired range. While the positional difference is ideally not present at all, the above predetermined range is a positional difference permissible range within which the reflective sensor 1 has a desired accuracy in position detection. The predetermined range can be set by a person skilled in the art in view of, for example, optical properties of the individual members of the optical system A. The predetermined range may be set on the basis of optical properties (properties with respect to the sub scanning direction) of a lens for use in a conventional reflective sensor.

Figure 5:
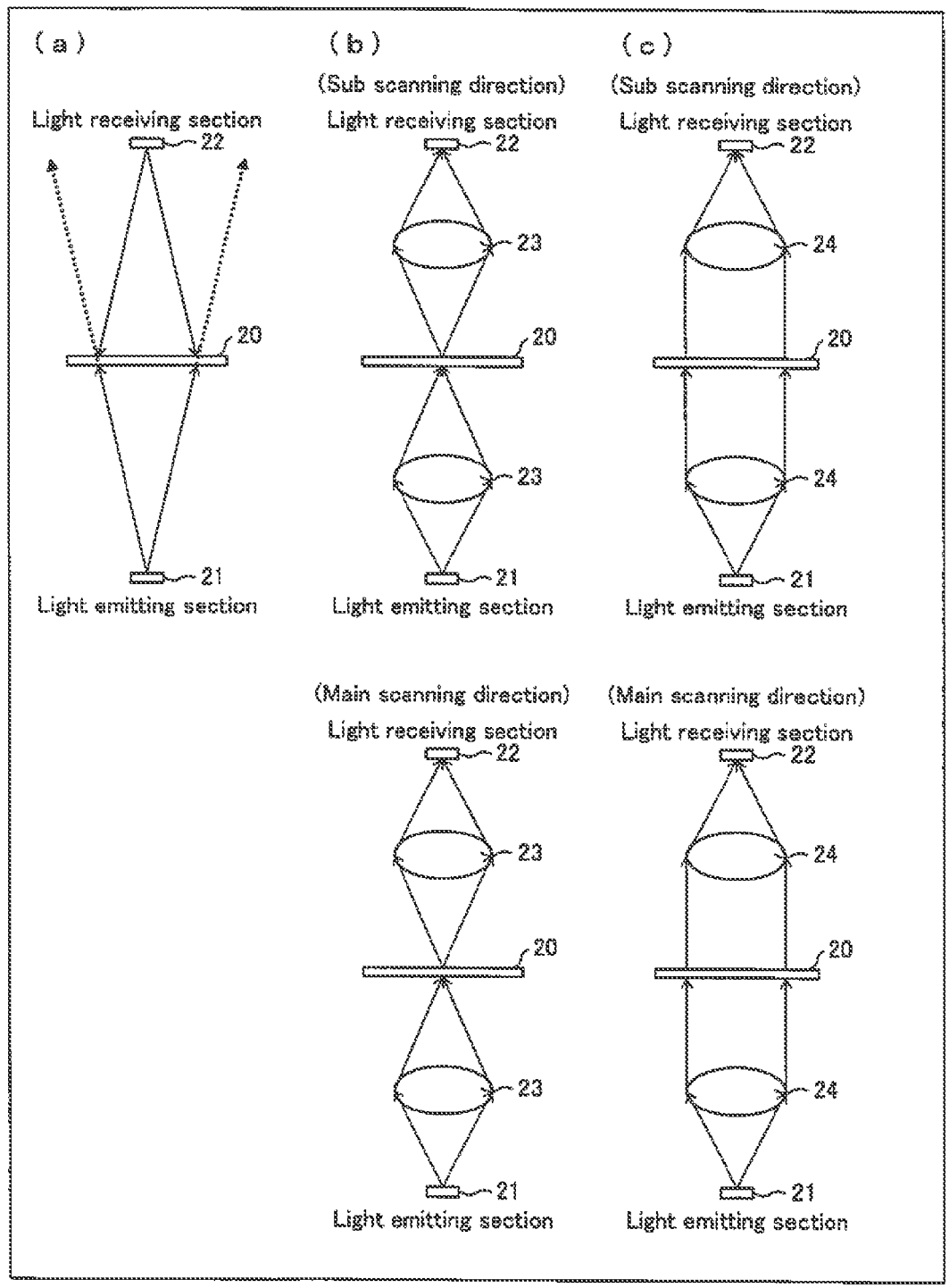
FIG. 5 shows diagrams each illustrating an optical system provided for a conventional reflective sensor.

The description below deals with the optical system A in detail. FIG. 5 shows diagrams each illustrating an optical system provided for a conventional reflective sensor. With reference to FIG. 5, the description below first deals with the relationship between (i) lenses disposed on an optical path, (ii) position detection accuracy, and (iii) robustness against a distance change and angle change.

Figure 21:
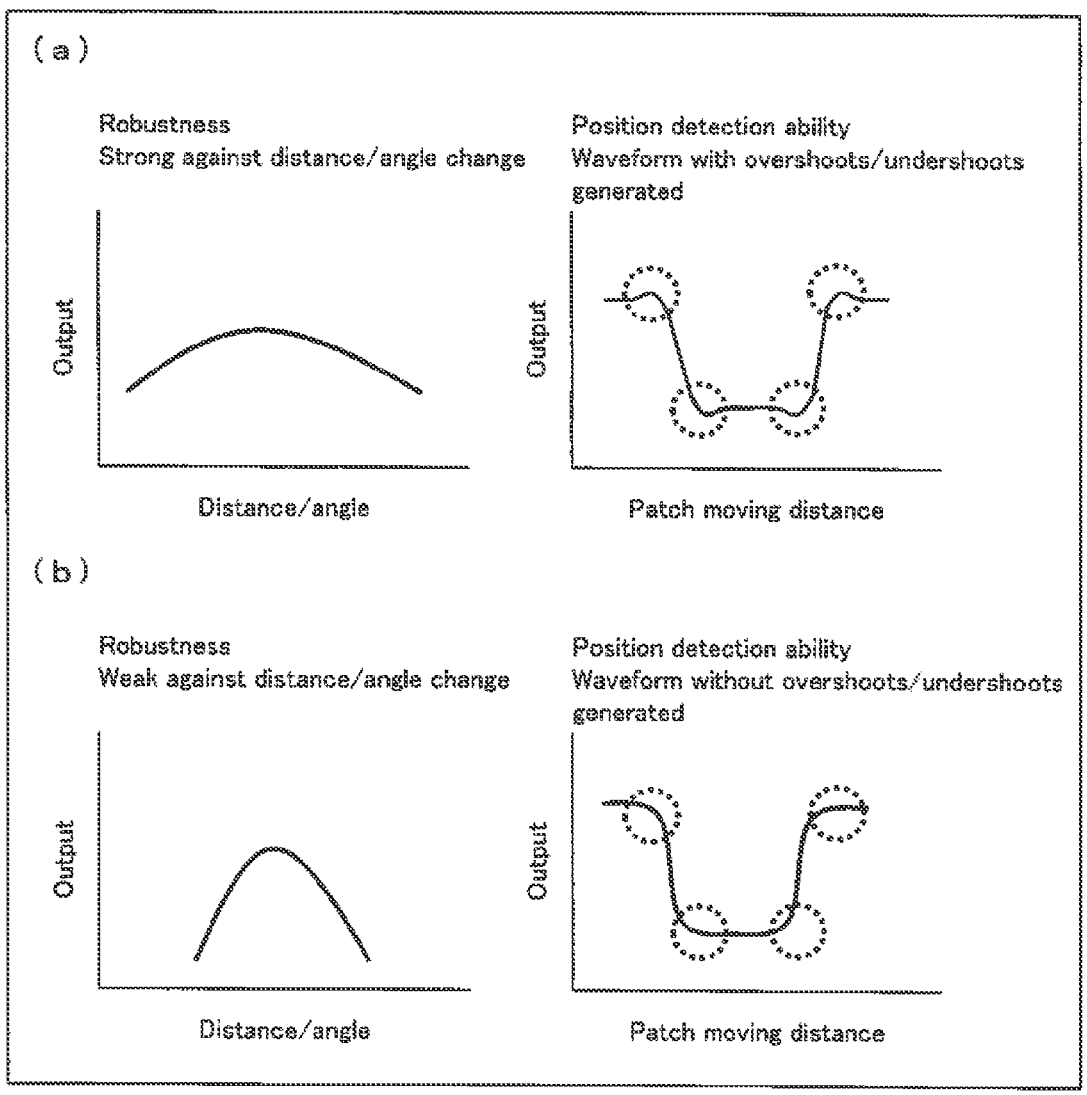
FIG. 21 shows explanatory graphs illustrating a relationship between robustness and position detection accuracy of a conventional reflective sensor.

(a) of FIG. 5 illustrates an optical system including no lens on an optical path of light that is emitted by a light emitting section 21 and that is then reflected by a detection target object 20 to reach a light receiving section for receiving regularly reflected light. This optical system has a diffuse-reflected light receiving area far wider than the regularly reflected light receiving area. The optical system thus unfortunately produces an output voltage having a waveform with overshoots and undershoots as discussed with reference to FIG. 21. The optical system illustrated in (a) of FIG. 5 will have low accuracy in position detection as a result. The reflective sensor, on the other hand, has high robustness against both a distance change and angle change since the optical system does not concentrate light onto a detection target object 20.

(b) of FIG. 5 illustrates an optical system including a light collecting lens 23 on an outward portion of the optical path and another light collecting lens 23 on a return portion of the optical path, each of the light collecting lenses 23 serving to concentrate light onto a detection target object 20. This optical system sufficiently condenses light in the sub scanning direction and the main scanning direction, so that the light receiving section 22 has a regularly reflected light receiving area and a diffuse-reflected light receiving area that substantially coincide with each other. This reflective sensor is less likely affected by diffuse-reflected light and has high accuracy in position detection as a result.

(c) of FIG. 5 illustrates an optical system including a collimating lens 24 on an outward portion of the optical path and another collimating lens 24 on a return portion of the optical path. This optical system collimates light in the sub scanning direction and the main scanning direction, so that the light receiving section 22 has a regularly reflected light receiving area and a diffuse-reflected light receiving area that substantially coincide with each other. This reflective sensor is less likely affected by diffuse-reflected light and has high accuracy in position detection as a result.

Figure 6:
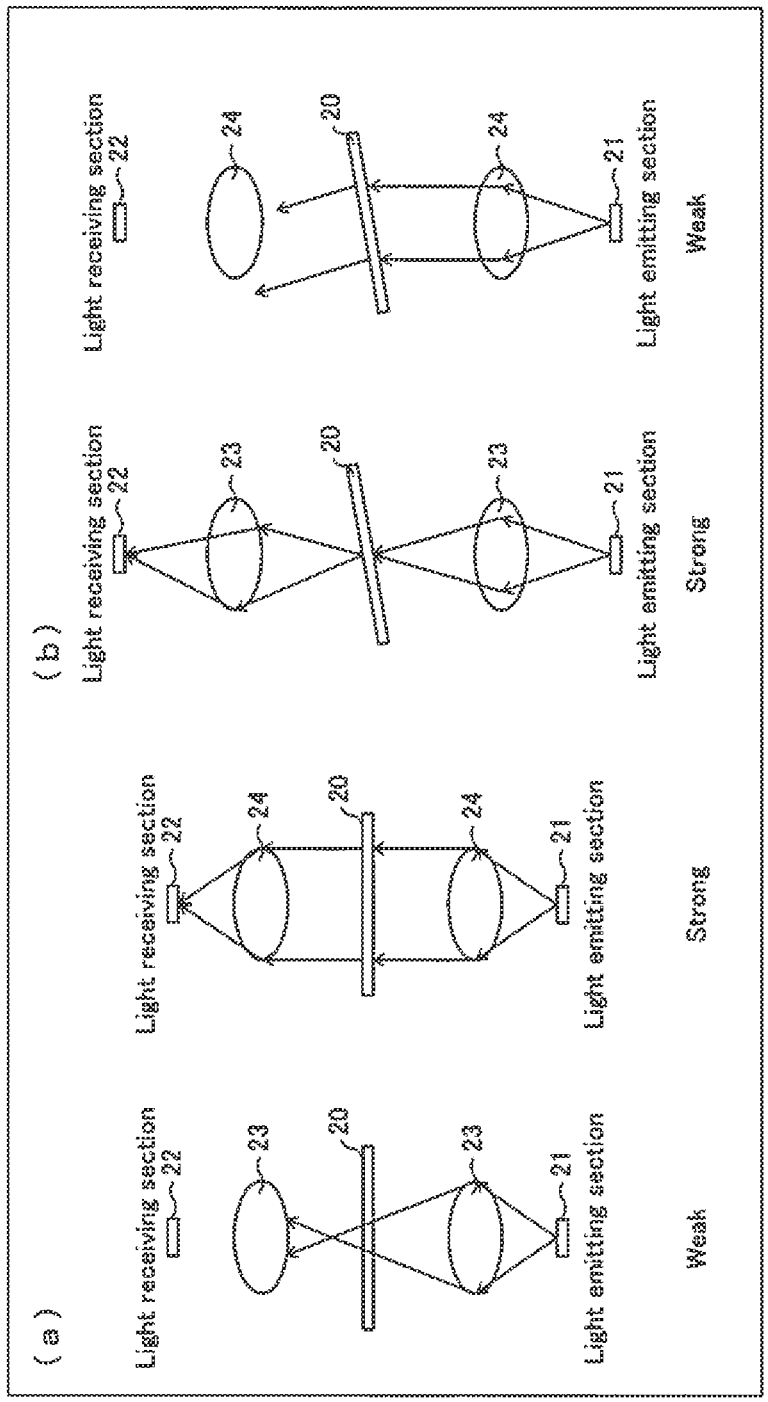
FIG. 6 shows diagrams each illustrating robustness of a conventional reflective sensor. (a) of FIG. 6 illustrates robustness against a distance change. (b) of FIG. 6 illustrates robustness against an angle change.

(a) of FIG. 6 shows diagrams illustrating robustness against a distance change. (b) of FIG. 6 shows diagrams illustrating robustness against an angle change. (a) and (b) of FIG. 6 each illustrate (i) on the left side, an optical system corresponding to that of (b) FIG. 5 and (ii) on the right side, an optical system corresponding to that of (c) of FIG. 5. (a) of FIG. 6 illustrates a distance change in which a detection target object 20 becomes closer to the light emitting section 21 and the light receiving section 22.

An optical system such as that illustrated on the left side of (b) of FIG. 6, which optical system concentrates light onto a detection target object 20, allows the light receiving section 22 to receive at least a certain amount of light even in the case where the angle of the detection target object 20 is changed. This optical system is strong against an angle change as a result. A distance change, however, decreases the amount of light received by the light receiving section 22 as illustrated on the left side of (a) of FIG. 6. This optical system is weak against a distance change as a result.

An optical system such as that illustrated on the right side of (a) of FIG. 6, which optical system collimates light onto a detection target object 20, allows the light receiving section 22 to receive at least a certain amount of light even in the case where the distance between the detection target object 20 and a reference position is changed. This optical system is strong against a distance change as a result. An angle change, however, decreases the amount of light received by the light receiving section 22 as illustrated on the right side of (b) of FIG. 6. This optical system is weak against an angle change as a result.

Figure 7:
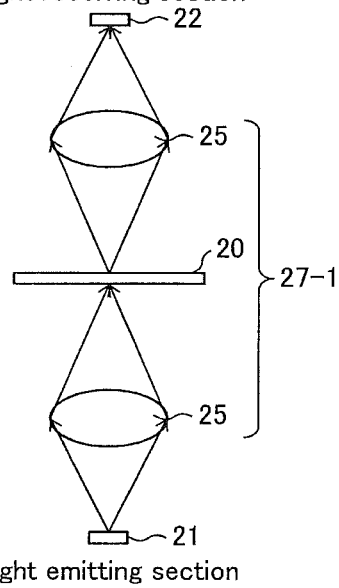
FIG. 7 is a diagram illustrating an optical system A included in the reflection sensor.
Figure 7:
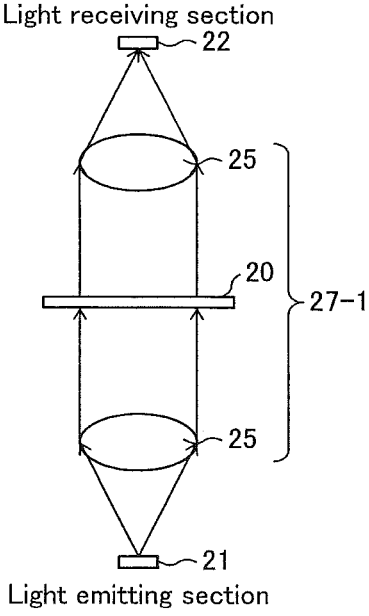

The optical system A mounted in the reflective sensor 1 combines the respective advantages of the conventional optical systems illustrated in (b) and (c) of FIG. 5. FIG. 7 illustrates an example configuration 27-1 for the optical system A included in the reflective sensor 1. The example of FIG. 7 includes a lens 25 on an outward portion of the optical path and another lens 25 on a return portion of the optical path, each of the lenses 25 serving to collect light in the sub scanning direction and collimate light in the main scanning direction.

This optical system condenses light in the sub scanning direction and collimates light in the main scanning direction, so that the light receiving section 22 has, for light from the light emitting section 21, a regularly reflected light receiving area and a diffuse-reflected light receiving area that substantially coincide with each other. The optical system is less likely affected by diffuse-reflected light and has high accuracy in position detection as a result. Regarding robustness, since the optical system does not condense light in the main scanning direction but does condense light in the sub scanning direction, the optical system allows the light receiving section 22 to receive at least a certain amount of light in the sub scanning direction as illustrated on the left side of (b) of FIG. 6. The optical system is, as a result, strong against an angle change in the sub scanning direction as compared to the optical system of (c) of FIG. 5, which does not condense light in sub scanning direction or the main scanning direction. Further, the optical system, which condenses light in the sub scanning direction, does not condense light in the main scanning direction. The optical system thus allows the light receiving section 22 to receive at least a certain amount of light in the main scanning direction as illustrated on the right side of (a) of FIG. 6. The optical system is, as a result, strong against a distance change as compared to the optical system of (b) of FIG. 5, which condenses light in both the sub scanning direction and the main scanning direction.

While the optical system of FIG. 7 collimates light in the main scanning direction, it may alternatively collect light in the main scanning direction as well. The optical system can be strong against a distance change as compared to that of (b) of FIG. 5 as long as the light receiving section 22 has a light receiving area (which includes a regularly reflected light receiving area and a diffuse-reflected light receiving area) for light from the light emitting section 21 which light receiving area is wider in the main scanning direction than in the sub scanning direction (in which the optical system collects light) even if the optical system collects light in the main scanning direction.

Figure 8:
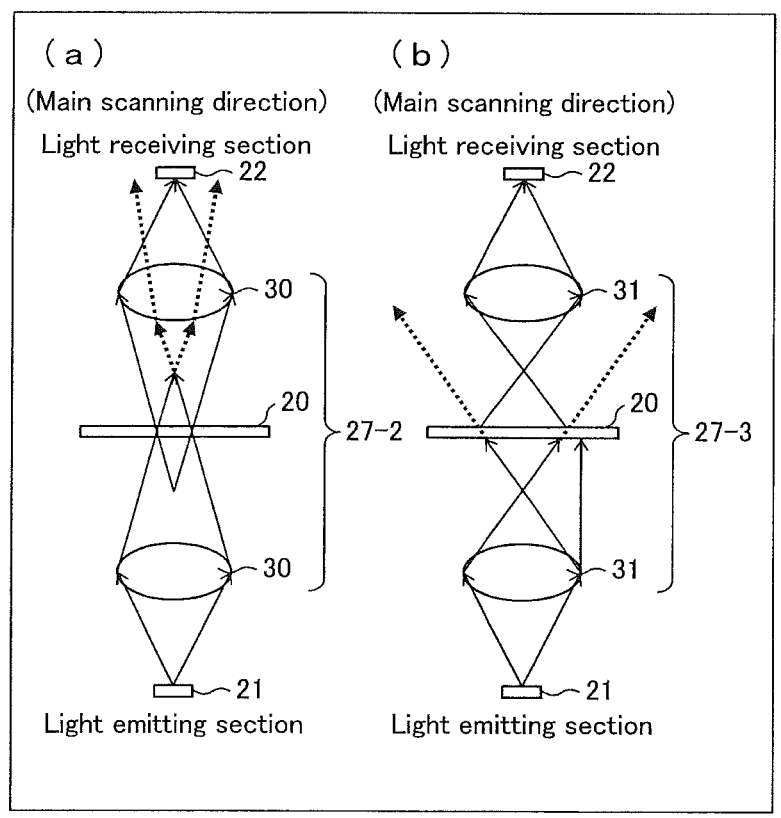
FIG. 8 shows diagrams each illustrating a modification of the optical system A.

FIG. 8 illustrates example configurations 27-2 and 27-3 for the optical system A. The configuration 27-2 includes lenses 30, whereas the configuration 27-3 includes lenses 31, the lenses 30 and 31 each serving to collect light in both the sub scanning direction and the main scanning direction. FIG. 8 shows illustrations for the main scanning direction. The configurations 27-2 and 27-3 are identical to the configuration 27-1 of FIG. 7 in the sub scanning direction. (a) of FIG. 8 illustrates an example including lenses 30 each (i) having a focal distance in the main scanning direction which focal distance is longer than that in the sub scanning direction (see FIG. 7), in which an image is formed on a detection target object 20, and thus (ii) forming an image at a position beyond the detection target object 20. (b) of FIG. 8 illustrates an example including lenses 31 each (i) having a focal distance in the main scanning direction which focal distance is shorter than that in the sub scanning direction (see FIG. 7), in which an image is formed on a detection target object 20, and thus (ii) forming an image at a position between the lens 31 and the detection target object 20.

The lenses 31 illustrated in (b) of FIG. 8 (each of which forms an image between a detection target object 20 and itself) each (i) have a larger curvature than the lenses 30 illustrated in (a) of FIG. 8 (each of which forms an image beyond a detection target object 20) and (ii) require a greater cost than the lenses 30. Thus, in the case where the optical system A is arranged to collect light in the main scanning direction as well, the optical system A preferably includes lenses each serving to collect light in the main scanning direction more weakly than in the sub scanning direction.

Figure 9:
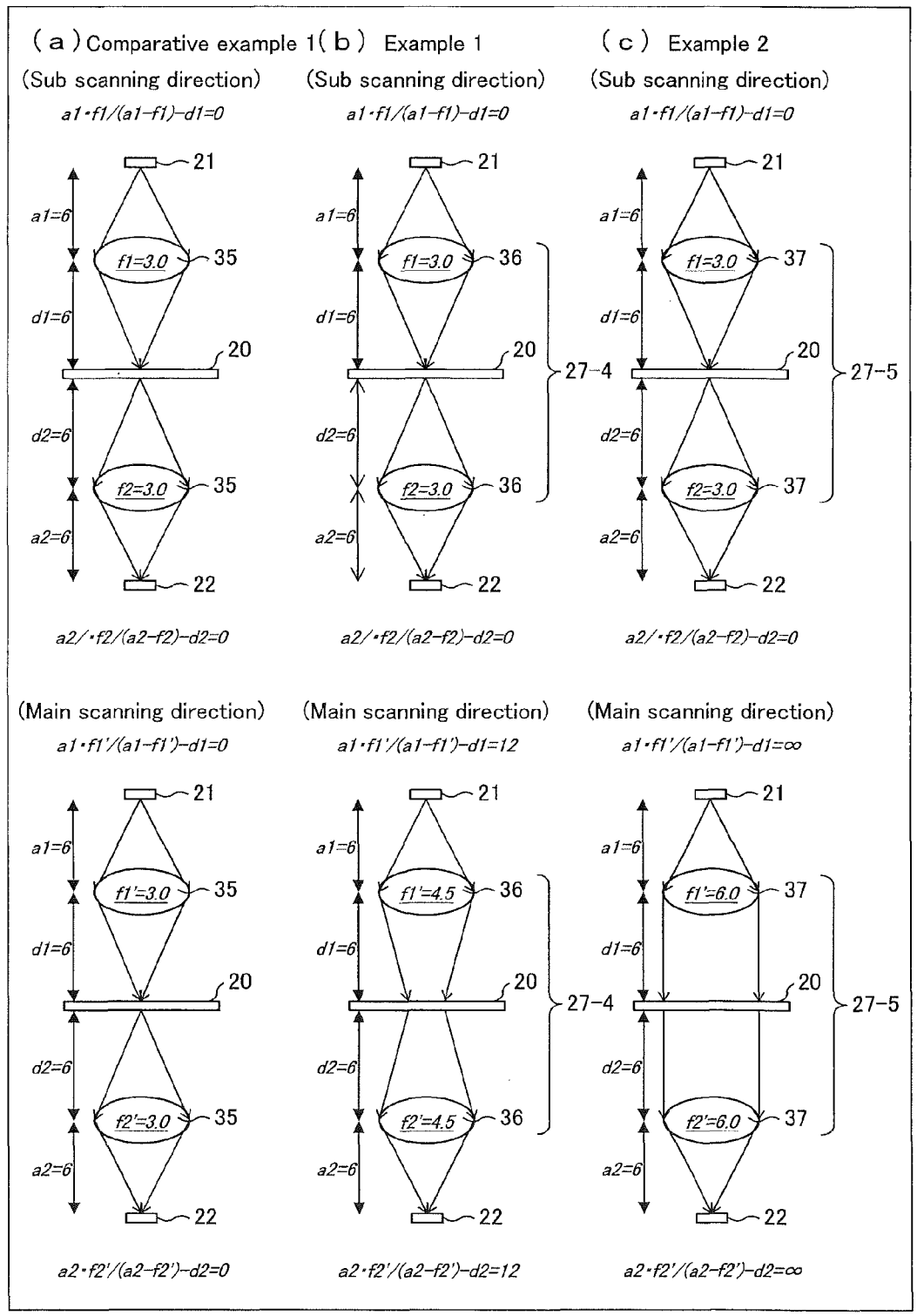
FIG. 9 shows diagrams each illustrating conditions that the optical system A is required to satisfy in order to collect light in a sub scanning direction and also collect light in a main scanning direction more weakly than in the sub scanning direction. (a) of FIG. 9 illustrates Comparative Example 1. (b) of FIG. 9 illustrates Example 1. (c) of FIG. 9 illustrates Example 2.

With reference to FIG. 9, the description below deals with conditions required in the case where the optical system A is arranged to collect light in the sub scanning direction and also collect light in the main scanning direction more weakly than in the sub scanning direction.

(a) of FIG. 9 illustrates Comparative Example 1. This Comparative Example 1 includes a lens section 35 on an outward portion of the optical path and another lens section 35 on a return portion of the optical path. The lens sections 35 each have a focal distance $f1$ of 3.0 in the sub scanning direction and a focal distance $f1'$ of 3.0 in the main scanning direction. With $d=6.0$ (where d represents the distance between the center of a lens section and a detection target object 20) and $a=6.0$ (where a represents the distance between the center of a lens section and the light receiving section 22 or light emitting section 21), both of $a \cdot f/(a-f)-d$ and $a \cdot f'/(a-f')-d$ return 0 according to the lens equation. The expression $a \neq f/(a-f)-d$ corresponds to the amount of mispositioning along the optical axis between a detection target object and the position at which an image is formed by a lens section in the sub scanning direction. The expression $a \cdot f'(a-f')-d$ corresponds to the amount of mispositioning along the optical axis between a detection target object and the position at which an image is formed by a lens section in the main scanning direction.

(b) of FIG. 9 illustrates Example 1. This Example 1 includes a lens section 36 on an outward portion of the optical path and another lens section 36 on a return portion of the optical path. The lens sections 36 each have a focal distance $f1$ of 3.0 in the sub scanning direction and a focal distance $f1'$ of 4.5 in the main scanning direction. With the same distance d as in Comparative Example 1 and the same distance a as in Comparative Example 1, $a \cdot f/(a-f)-d$ returns 0 while $a \cdot f'(a-f)-d$ returns 12. This indicates that the light emitting section 21 of Example 1 emits light that forms a spot having a diameter larger in the main scanning direction than in the sub scanning direction.

(c) of FIG. 9 illustrates Example 2. This Example 2 includes a lens section 37 on an outward portion of the optical path and another lens section 37 on a return portion of the optical path. The lens sections 37 each have a focal distance $f1$ of 3.0 and in the sub scanning direction and a focal distance $f1'$ of 6.0 in the main scanning direction. With the same distance d as in Comparative Example 1 and the same distance a as in Comparative Example 1, $a \cdot f/(a-f)-d$ returns 0 while $a \cdot f'/(a-f')-d$ returns $\infty$. This indicates that the light emitting section 21 of Example 2 emits light that forms a spot having a diameter larger in the main scanning direction than in the sub scanning direction.

As described above, the lens equation shows that an optical system needs to satisfy $0 \leq a \cdot f/(a-f)-d$ to collect light in the sub scanning direction. The expression $a \cdot f/(a-f)-d$ in the above formula corresponds to the amount of mispositioning along the movement direction between a detection target object and the position at which an image is formed by a lens section. The above formula shows that the amount of the above mispositioning is 0 or greater. This indicates that the above optical system has a wide range of light collecting performance in the sub scanning direction which range covers from (i) collecting light completely for formation of an image on a detection target object to (ii) collecting light incompletely by condensing light further than collimating light for formation of an image at a position beyond the detection target object.

The lens equation further shows that an optical system needs to satisfy $0 < a \cdot f'/(a-f')-d$ or $a \cdot f'/(a-f')-d = \infty$ and also satisfy $a \cdot f/(a-f)-d < a \cdot f'/(a-f')-d$ to collect light not only in the sub scanning direction but also in the main scanning direction more weakly than in the sub scanning direction.

As described above, the expression $a \cdot f/(a-f)-d$ corresponds to the amount of mispositioning between a detection target object and the position at which an image is formed by a lens section in the sub scanning direction, whereas the expression $a \cdot f'/(a-f')-d$ corresponds to the amount of mispositioning between a detection target object and the position at which an image is formed by a lens section in the main scanning direction. The equation a·f'/(a−f')−d=∞ indicates a lens section that does not collect light but collimates light in the main scanning direction. Satisfying the above equation reliably allows the light receiving section 22 to have a light receiving area that is wider in the main scanning direction than in the sub scanning direction.

The above conditions for an optical system may alternatively be satisfied by including only one lens section on either an outward portion of the optical path or a return portion of the optical path. The conditions are, however, preferably satisfied by including a lens section on an outward portion of the optical path and another lens section on a return portion of the optical path. Including two lens sections respectively on an outward portion and return portion of the optical path allows a light receiving section to have, for light from a light emitting section, a regularly reflected light receiving area and a diffuse-reflected light receiving area that coincide with each other more accurately. This allows a reflective sensor to have further improved accuracy in position detection.

Figure 10:
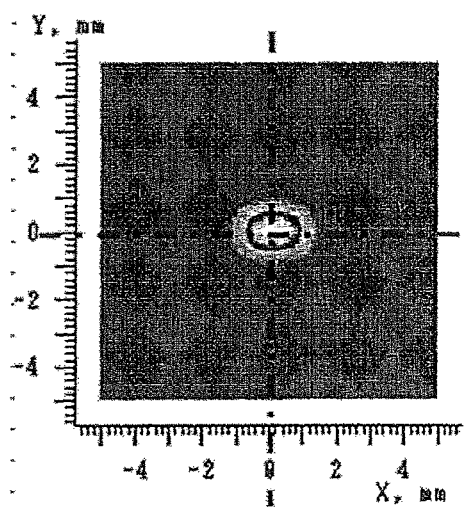
FIG. 10 shows an explanatory graph illustrating a shape of a spot formed by an anamorphic lens usable as an optical lens included in the reflective sensor.
Figure 10:
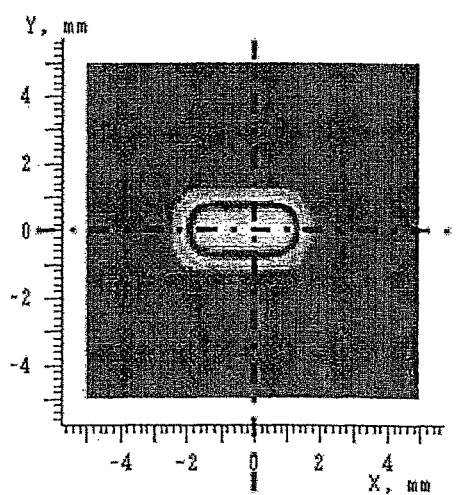

An optical system may further alternatively include (i) on only one of an outward portion of the optical path and a return portion of the optical path, a single lens section that satisfies the above conditions and (ii) a collimating lens on the other portion of the optical path. However, in the case where an optical system includes a collimating lens on one of an outward portion of the optical path and a return portion of the optical path, such an optical system will be weak in the sub scanning direction against an angle change of a detection target object along its movement direction (discussed above as a problem related to the environment in which an optical system is used). This indicates that regarding the sub scanning direction, in the case where an optical system includes, on each of an outward portion and return portion of the optical path, a condensing lens that satisfies the above conditions, the optical system will be improved in terms of both accuracy in position detection and sub scanning angle FIG. 10 shows an explanatory graph illustrating a shape of a spot formed by an anamorphic lens usable as any of the lenses 25, 30, and 31 and lens sections 36 and 37 of the optical system A. The shape of a spot formed by the anamorphic lens is larger in one of two directions orthogonal to each other than in the other as compared to the shape of a spot formed by a symmetric spherical lens shown for reference. The anamorphic lens is so oriented as to form a spot having a longer axis direction along the main scanning direction and a shorter axis direction along the sub scanning direction. The anamorphic lens, which forms a spot having a diameter shown in FIG. 10, has a curved surface, which has an origin corresponding to the vertex of the anamorphic lens.

Figure 11:
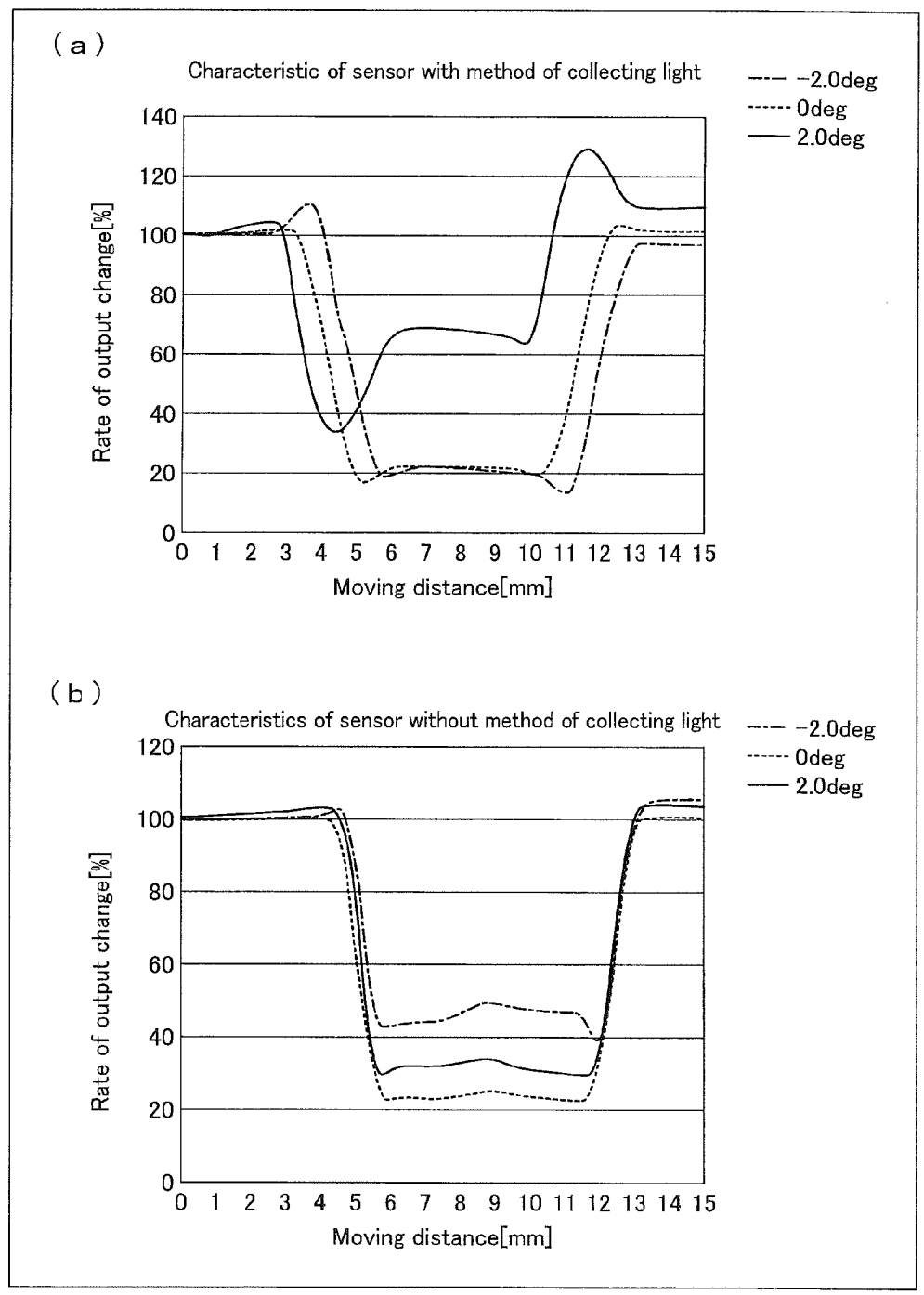
FIG. 11 shows graphs each illustrating how the light collection property of a lens is related to a detected waveform corresponding to a change in the angle of a detection target object.

FIG. 11 shows graphs each illustrating how the light collection property of a lens is related to a detected waveform corresponding to a change in the angle of a detection target object. (a) of FIG. 11 illustrates characteristics of a sensor using no collecting light method for the sub scanning direction or the main scanning direction. (b) of FIG. 11 illustrates characteristics of a sensor using a collecting light method for only the sub scanning direction. As illustrated in (a) of FIG. 11, in the case where a sensor uses no collecting light method for the sub scanning direction or the main scanning direction, a change in the angle of a detection target object unfortunately disturbs the waveform. In contrast, as illustrated in (b) of FIG. 11, in the case where a sensor uses a collecting light method even for only the sub scanning direction, a change in the angle of a detection target object does not disturb the waveform.

Figure 12:
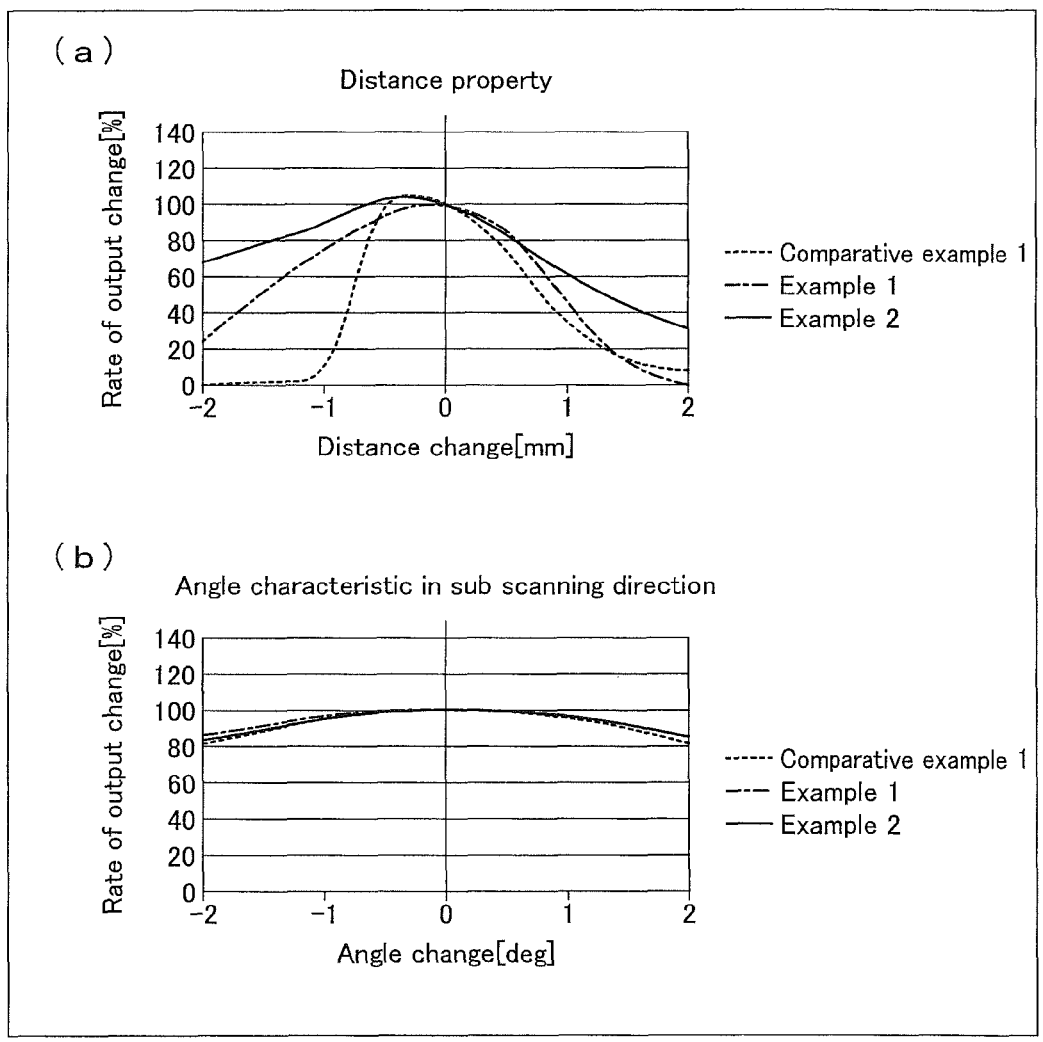
FIG. 12 shows graphs each illustrating respective robustness properties of Comparative Example 1 and Examples 1 and 2 illustrated in FIG. 9.

FIG. 12 shows graphs each illustrating respective robustness properties of Comparative Example 1 and Examples 1 and 2 illustrated in FIG. 9. (a) of FIG. 12 indicates that as compared to Comparative Example 1 (which has a focal distance f' in the main scanning direction and a focal distance f in the sub scanning direction which focal distances f' and f are equal to each other), Examples 1 and 2 (each of which has a focal distance f' in the main scanning direction which focal distance f' is longer than a focal distance f in the sub scanning direction) each have improved distance characteristics as a longer focal distance f' results in a smoother curve. (b) of FIG. 12 indicates that for any of Comparative Example 1 and Examples 1 and 2, even changing the focal distance f' in the main scanning direction does not change the angle characteristics in the sub scanning direction. Comparative Example 1 and Examples 1 and 2, on the other hand, showed that a longer focal distance f' in the main scanning direction than a focal distance f in the sub scanning direction tends to result in slightly poorer angle characteristics in the main scanning direction. Such slightly poorer angle characteristics in the main scanning direction, however, have been confirmed not problematic in, for example, an image forming apparatus including the reflective sensor 1.

In the case where the reflective sensor 1 is mounted in the image forming apparatus 51 to detect, as a detection target object 20, a toner image on the transfer belt 56 as illustrated in FIG. 4, it is important for the reflective sensor 1 to have good angle characteristics in the sub scanning direction. This is due to the structure of the transfer belt 56 (on which a toner image is formed) being provided around the pair of rollers 67 and 68 in a tensioned state. On the transfer belt 56 arranged as such, the toner image easily has an angle change in the sub scanning direction as a result of, for example, a deflection of the belt, but hardly has an angle change in the main scanning direction, along which the roller 67 is disposed inside the transfer belt 56. Even if the toner image has an angle change in the main scanning direction, such an angle change is very small. This indicates that slightly poorer angle characteristics in the main scanning direction are not problematic unlike in the sub scanning direction.

With reference to FIGS. 13 through 16, the description below deals with other example configurations 27-6 through 27-9 of the optical system A and their respective robustness properties.

Figure 13:
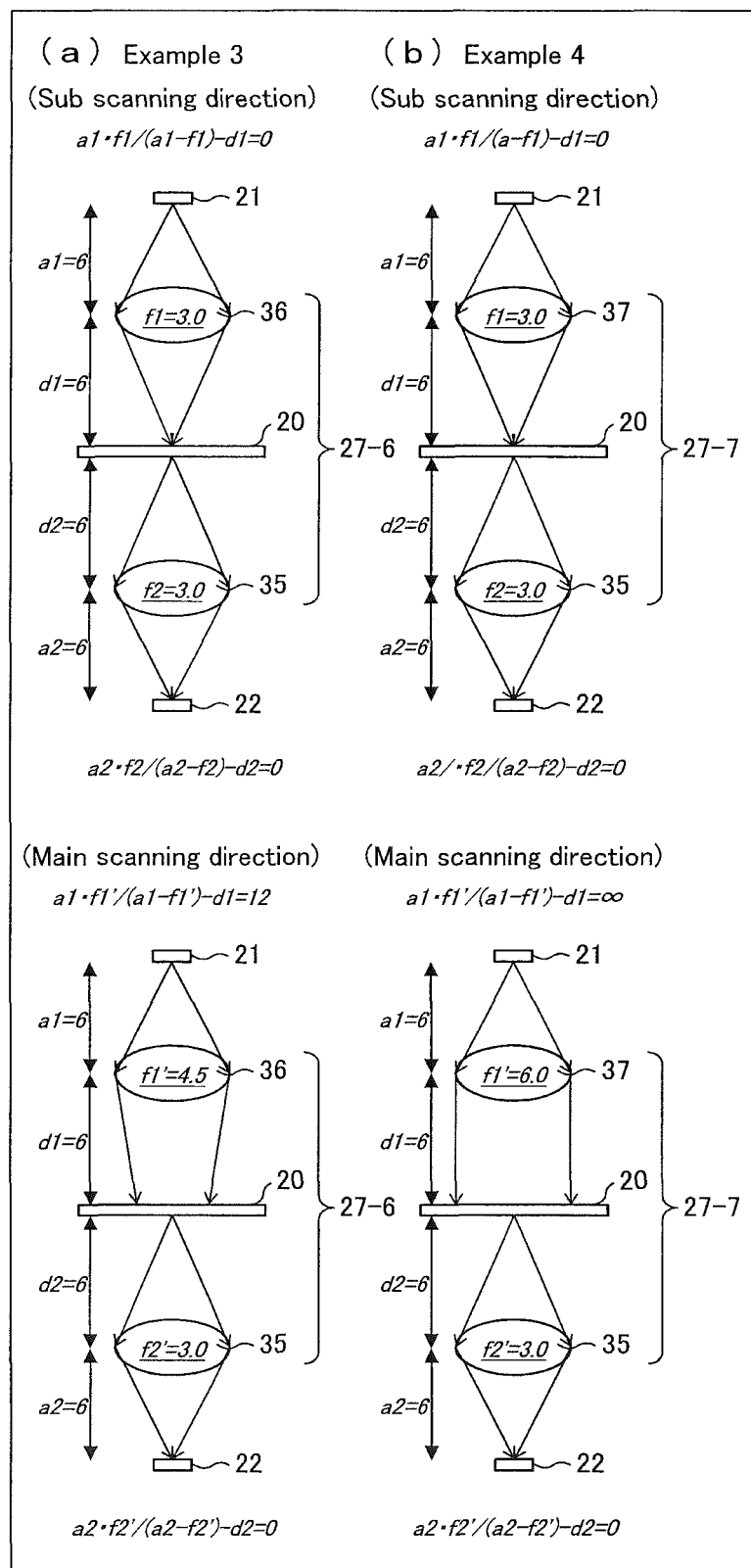
FIG. 13 illustrates example configurations of the optical system A. (a) of FIG. 13 illustrates Example 3. (b) of FIG. 13 illustrates Example 4.
Figure 14:
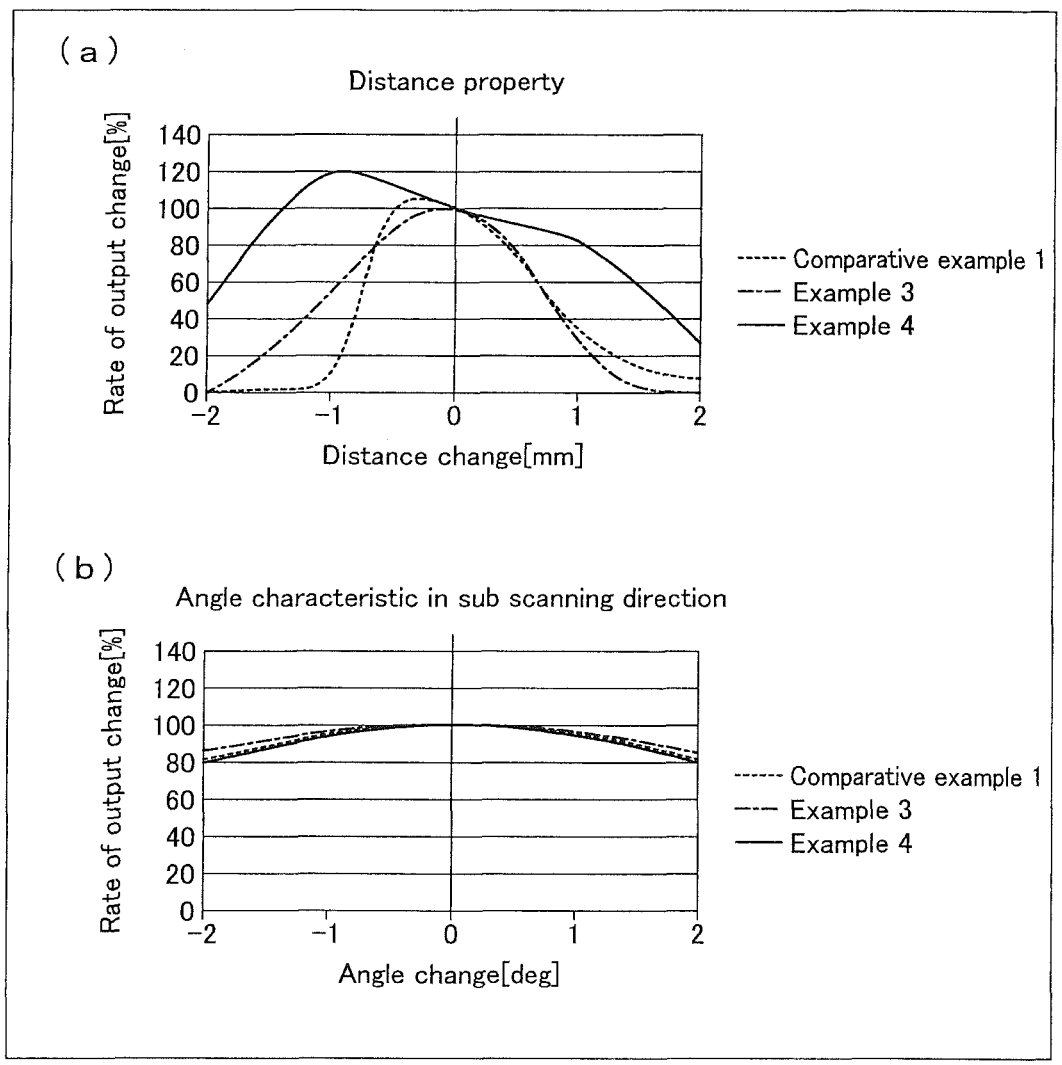
FIG. 14 shows graphs each illustrating respective robustness properties of Examples 3 and 4 illustrated in FIG. 13.

(a) of FIG. 13 illustrates Example 3. This Example 3 (example configuration 27-6) is identical to Comparative Example 1 except that the lens section 35 disposed on the outward portion of the optical path is replaced with a lens section 36. The lens section 36 has a focal distance f1 of 4.5 in the sub scanning direction and a focal distance f1' of 4.5 in the main scanning direction. (b) of FIG. 13 illustrates Example 4. This Example 4 (example configuration 27-7) is identical to Comparative Example 1 except that the lens section 35 disposed on the outward portion of the optical path is replaced with a lens section 37. The lens section 37 has a focal distance f1 of 6.0 in the sub scanning direction and a focal distance f1' of 6.0 in the main scanning direction. FIG. 14 shows graphs each illustrating respective robustness properties of Comparative Example 1 and Examples 3 and 4. FIG. 14 indicates that Examples 3 and 4 each have an improved robustness property over Comparative Example 1.

Figure 15:
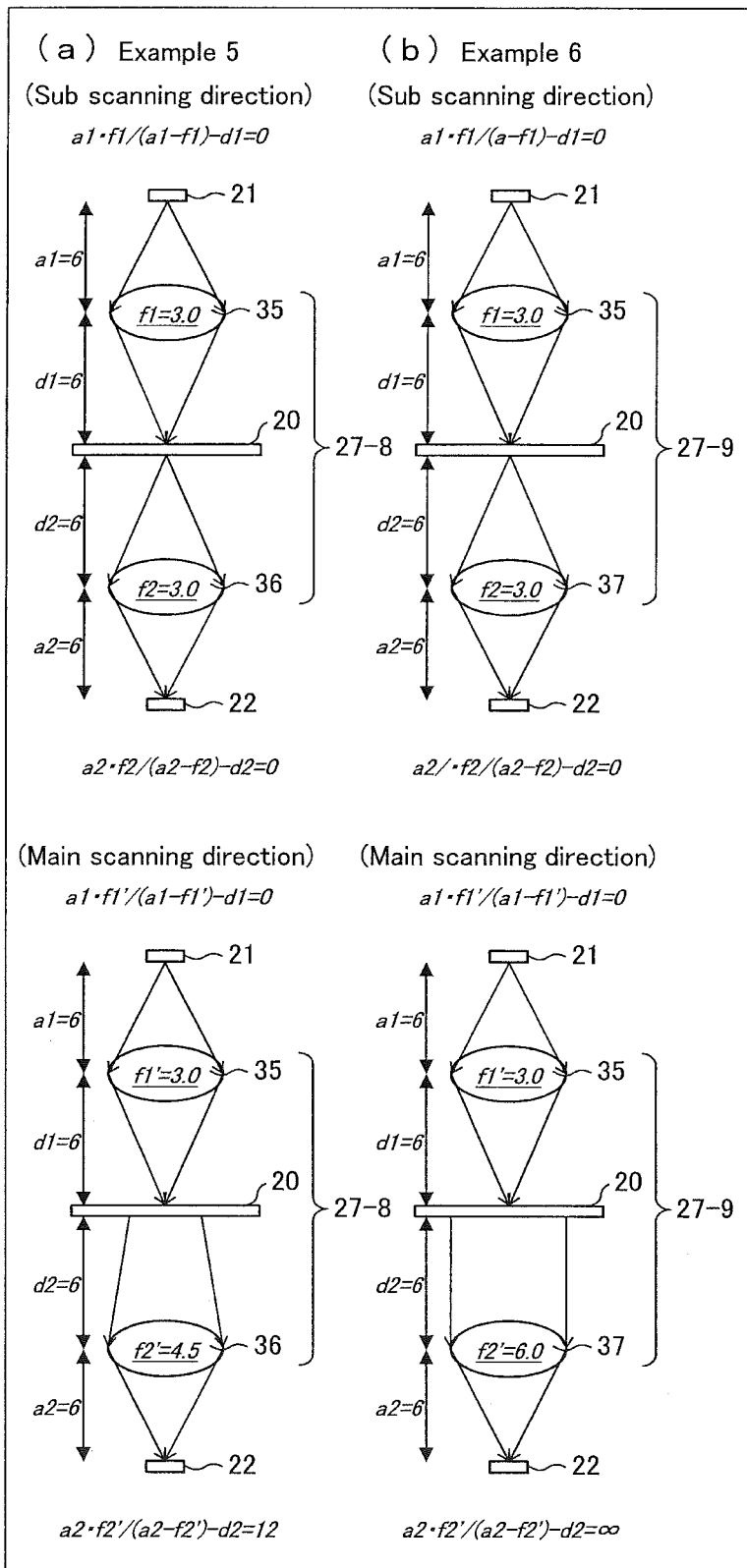
FIG. 15 illustrates example configurations of the optical system A. (a) of FIG. 15 illustrates Example 5. (b) of FIG. 15 illustrates Example 6.
Figure 16:
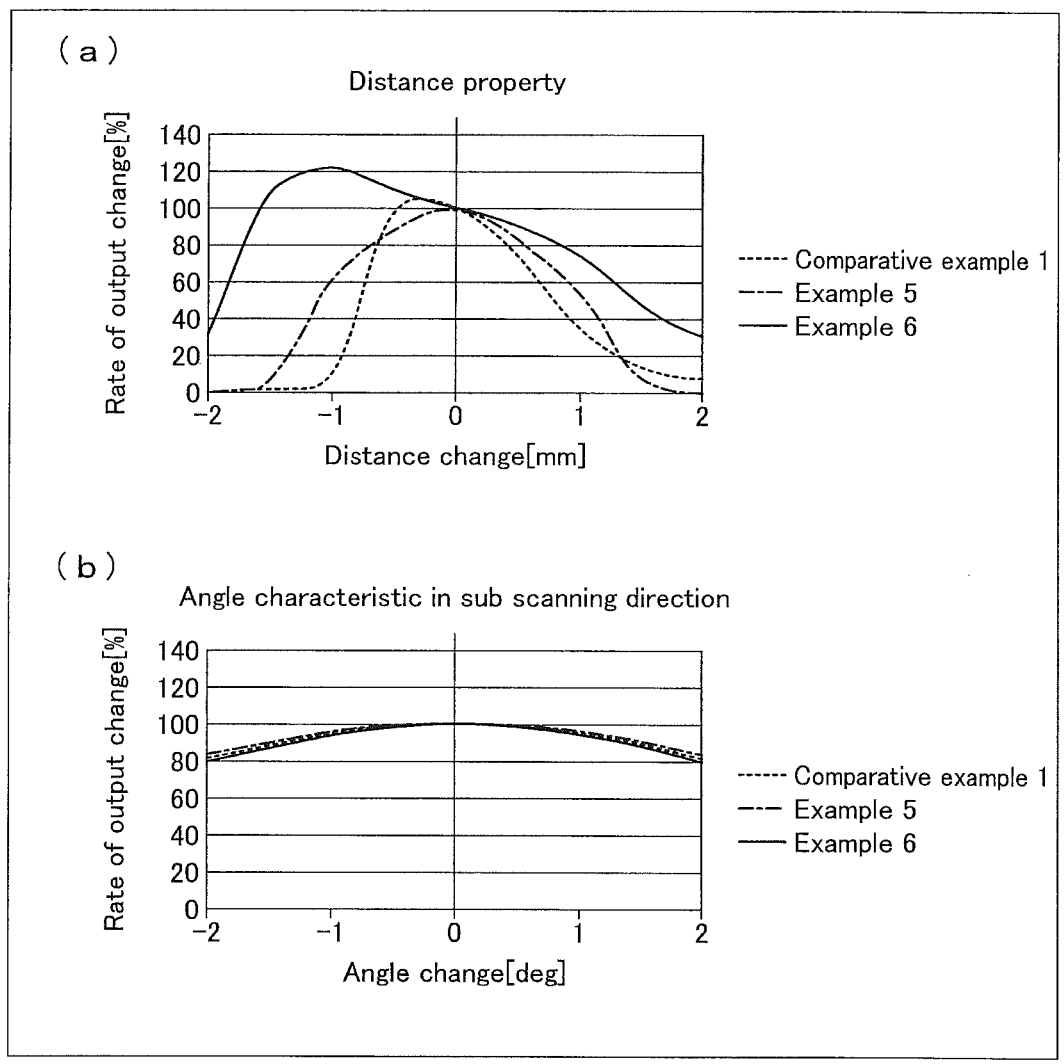
FIG. 16 shows graphs each illustrating respective robustness properties of Examples 5 and 6 illustrated in FIG. 15.

(a) of FIG. 15 illustrates Example 5. This Example 5 (example configuration 27-8) is identical to Comparative Example 1 except that the lens section 35 disposed on the return portion of the optical path is replaced with a lens section 36. The lens section 36 has a focal distance f1 of 4.5 in the sub scanning direction and a focal distance f1' of 4.5 in the main scanning direction. (b) of FIG. 15 illustrates Example 6. This Example 6 (example configuration 27-9) is identical to Comparative Example 1 except that the lens section 35 disposed on the return portion of the optical path is replaced with a lens section 37. The lens section 37 has a focal distance f1 of 6.0 in the sub scanning direction and a focal distance f1' of 6.0 in the main scanning direction. FIG. 16 shows graphs each illustrating respective robustness properties of Comparative Example 1 and Examples 5 and 6. FIG. 16 indicates that Examples 5 and 6 each have an improved robustness property over Comparative Example 1.

With reference to FIGS. 17 through 20, the description below deals with an embodiment of a reflective sensor 1 including an optical system 27. This reflective sensor 1 is so provided as to detect, as detection target objects 20, a transfer belt 56 and toner patches P on the transfer belt 56.

Figure 17:
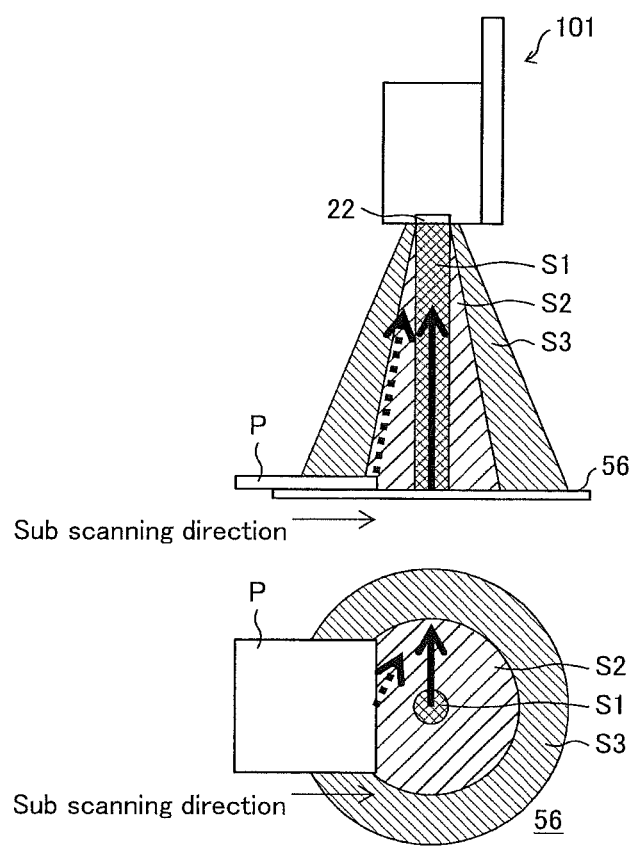
FIG. 17 shows explanatory diagrams illustrating an irradiation area, a regularly reflected light receiving area, and a diffuse-reflected light receiving area of a conventional reflection sensor including no lens.

FIG. 17 illustrates an irradiation area, a regularly reflected light receiving area, and a diffuse-reflected light receiving area of a conventional reflective sensor 101 including no lens (FIG. 17 corresponds to (a) of FIG. 5). Only a portion of the whole light receiving area of the light receiving section 22 corresponds to the regularly reflected light receiving area S1, over which the light receiving section 22 receives regularly reflected light (indicated by a thick arrow in FIG. 17). This unfortunately lets the light receiving section 22 receive unnecessary diffuse-reflected light (indicated by a broken arrow) while a toner patch P on the transfer belt 56 passes through the diffuse-reflected light receiving area S2, with the result of low accuracy in position detection. FIG. 17 shows the reference sign "S3" to indicate the area within which the light emitting section emits light.

Figure 18:
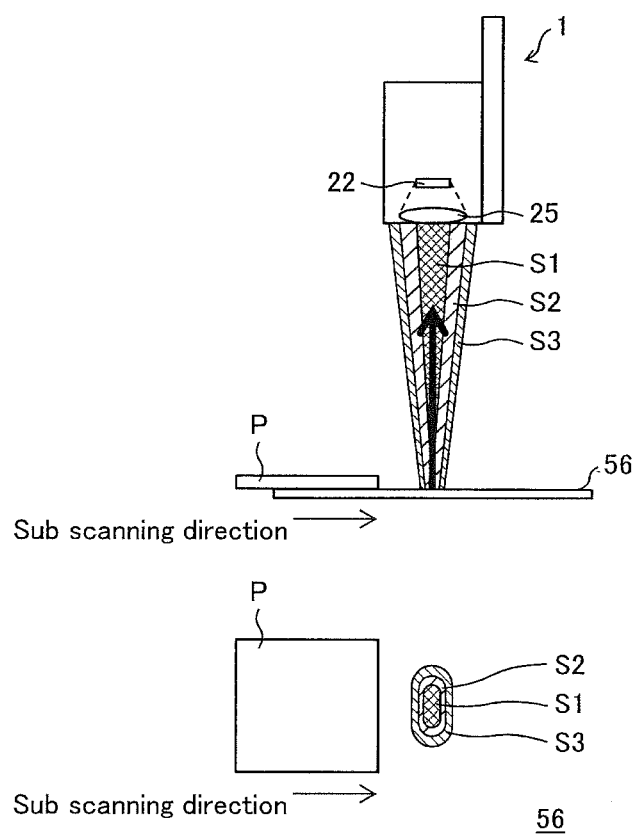
FIG. 18 shows explanatory diagrams illustrating an irradiation area, a regularly reflected light receiving area, and a diffuse-reflected light receiving area of a reflective sensor of an embodiment including an optical system A that includes two lenses on both an outward portion and return portion of an optical path.

FIG. 18 illustrates an irradiation area, a regularly reflected light receiving area, and a diffuse-reflected light receiving area of the reflective sensor 1 of an embodiment including an optical system A that includes two lenses disposed respectively on an outward portion and return portion of the optical path. FIG. 18 omits the lens 25 on the side of the light emitting section 21. This configuration allows the regularly reflected light receiving area S1, over which the light receiving section 22 receives regularly reflected light (indicated by a thick arrow), and the diffuse-reflected light receiving area S2 to substantially coincide with each other in the sub scanning direction (FIG. 18 shows a positional difference between the regularly reflected light receiving area S1 and the diffuse-reflected light receiving area S2 for convenience of illustration. This positional difference is, however, extremely small, and is ideally absent). This almost completely prevents the light receiving section 22 from receiving unnecessary diffuse-reflected light while a toner patch P passes through the diffuse-reflected light receiving area S2, with the result of high accuracy in position detection. Further, the reflective sensor 1 condenses light in the sub scanning direction and thus has high robustness against an angle change. The reflective sensor 1 does not condense light in the main scanning direction as much as in the sub scanning direction for a larger spot diameter. This arrangement allows the reflective sensor 1 to have robustness against a distance change which robustness is higher than that of a reflective sensor that condenses light in both the main scanning direction and the sub scanning direction. In addition, this reflective sensor 1 collects irradiation light to have an irradiation area S3 closer to the whole light receiving area of the light receiving section 22, with the result of high efficiency in light use.

Figure 19:
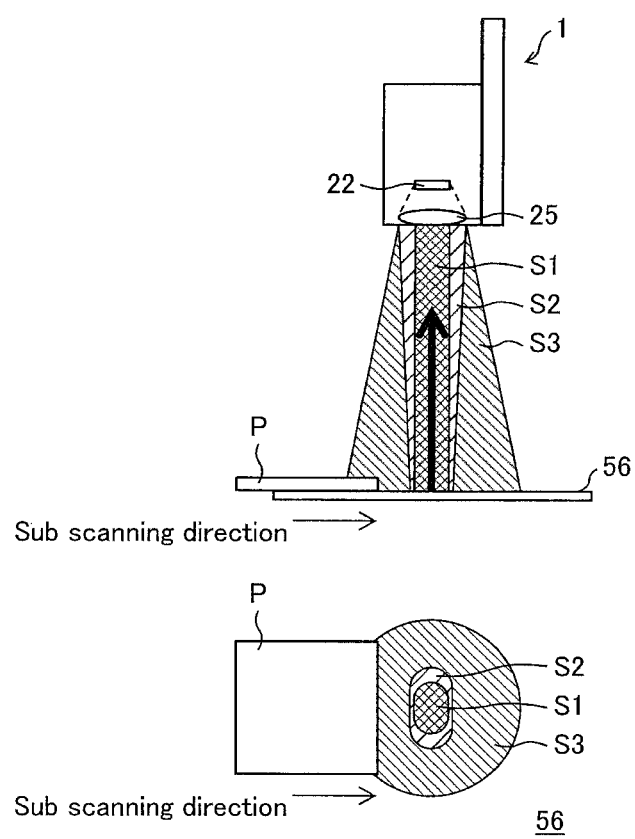
FIG. 19 shows explanatory diagrams illustrating an irradiation area, a regularly reflected light receiving area, and a diffuse-reflected light receiving area of a reflective sensor of an embodiment including an optical system A that includes a single lens on only a return portion of an optical path.

FIG. 19 illustrates an irradiation area, a regularly reflected light receiving area, and a diffuse-reflected light receiving area of the reflective sensor 1 of an embodiment including an optical system A that includes a single lens disposed on only a return portion of the optical path. This configuration allows the regularly reflected light receiving area S1, over which the light receiving section 22 receives regularly reflected light (indicated by a thick arrow), and the diffuse-reflected light receiving area S2 to substantially coincide with each other in the sub scanning direction (FIG. 19 also shows a positional difference between the regularly reflected light receiving area S1 and the diffuse-reflected light receiving area S2 for convenience of illustration. This positional difference is, however, extremely small, and is ideally absent). This allows for high accuracy in position detection as with the configuration illustrated in FIG. 18. Further, the reflective sensor 1 condenses light in the sub scanning direction and thus has high robustness against an angle change. The reflective sensor 1 does not condense light in the main scanning direction as much as in the sub scanning direction for a larger spot diameter. This arrangement, as with the arrangement illustrated in FIG. 18, allows the reflective sensor 1 to have robustness against a distance change which robustness is higher than that of a reflective sensor that condenses light in both the main scanning direction and the sub scanning direction.

Figure 20:
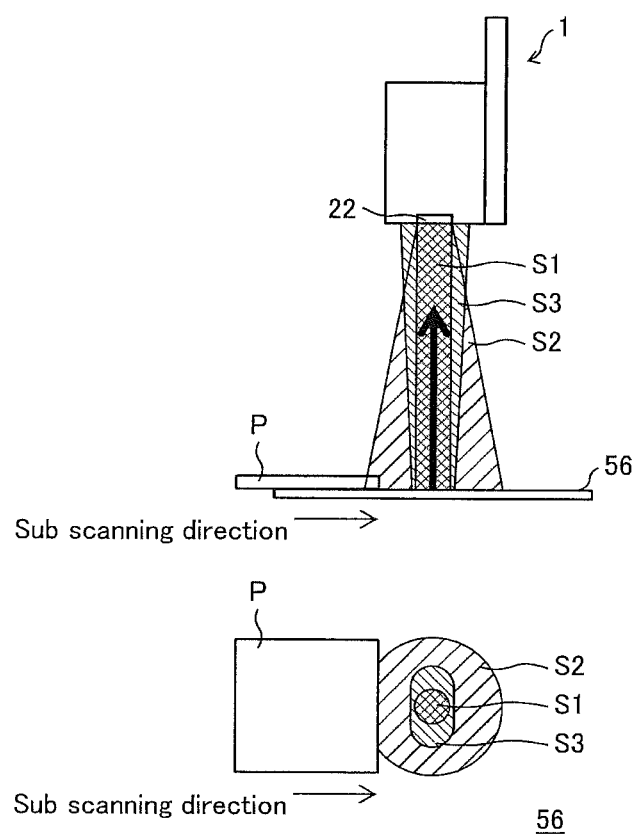
FIG. 20 shows explanatory diagrams illustrating an irradiation area, a regularly reflected light receiving area, and a diffuse-reflected light receiving area of a reflective sensor of an embodiment including an optical system A that includes a single lens on only an outward portion of an optical path.

FIG. 20 illustrates an irradiation area, a regularly reflected light receiving area, and a diffuse-reflected light receiving area of the reflective sensor 1 of an embodiment including an optical system A that includes a single lens disposed on only an outward portion of the optical path. FIG. 20 omits the lens 25 on the side of the light emitting section 21. This configuration condenses irradiation light on the side of the light emitting section, and thus allows the regularly reflected light receiving area S1, which is located in the irradiation area S3, and the diffuse-reflected light receiving area S2 to substantially coincide with each other (FIG. 20 also shows a positional difference between the regularly reflected light receiving area S1 and the irradiation area S3 for convenience of illustration. This positional difference is, however, extremely small, and is ideally absent). This allows for high accuracy in position detection as with the configuration illustrated in FIG. 18. Further, the reflective sensor 1 condenses light in the sub scanning direction and thus has high robustness against an angle change. The reflective sensor 1 does not condense light in the main scanning direction as much as in the sub scanning direction for a larger spot diameter. This arrangement, as with the arrangement illustrated in FIG. 18, allows the reflective sensor 1 to have robustness against a distance change which robustness is higher than that of a reflective sensor that condenses light in both the main scanning direction and the sub scanning direction. In addition, this reflective sensor 1 collects irradiation light, with the result of higher efficiency in light use than with the arrangement illustrated in FIG. 19.

As described above, a reflective sensor of the present invention includes: a light emitting section for emitting light toward a detection target object moving in a single direction; and a light receiving section for receiving regular reflection of the light, the reflective sensor further comprising: an optical system including at least one lens section each including at least one lens which at least one lens section is disposed on an optical path of light that (i) is emitted by the light emitting section, (ii) travels to the detection target object, (iii) is reflected by the detection target object, and (iv) reaches the light receiving section, the optical system being arranged to, in a movement direction in which the detection target object is moving, collect light so that a regularly reflected light receiving area differs in position from a diffuse-reflected light receiving area by an amount within a predetermined range, the regularly reflected light receiving area being an area present between (i) the detection target object and (ii) the light emitting section and the light receiving section within which area the light emitted by the light emitting section is regularly reflected by the detection target object and is then received by the light receiving section, the diffuse-reflected light receiving area being an area present between (i) the detection target object and (ii) the light emitting section and the light receiving section within which area the light emitted by the light emitting section is diffuse-reflected by the detection target object and is then received by the light receiving section, the optical system being further arranged to, in a perpendicular direction that is perpendicular to the movement direction, refract light so that a light receiving area, which covers the regularly reflected light receiving area and the diffuse-reflected light receiving area, is wider in the perpendicular direction than in the movement direction.

The above arrangement allows the optical system to, in the direction in which a detection target object is moving, collect light so that the light receiving section has, for light from the light emitting section, a regularly reflected light receiving area and a diffuse-reflected light receiving area that differ from each other in position within a predetermined range. The term "predetermined range" is a range set as appropriate so that the reflective sensor is capable of detecting the position of a detection target object with an accuracy that falls within a desired range. While the positional difference is ideally not present at all, the above predetermined range is a positional difference permissible range within which the reflective sensor has a desired accuracy in position detection.

The above arrangement thus allows the regularly reflected light receiving area and the diffuse-reflected light receiving area to substantially coincide with each other in the movement direction, which prevents an influence of diffuse-reflected light and results in high accuracy in position detection. The above arrangement further allows the optical system to, in a perpendicular direction that is perpendicular to the movement direction, refract light so that a light receiving area, which covers the regularly reflected light receiving area and the diffuse-reflected light receiving area, is wider in the perpendicular direction than in the movement direction. This arrangement allows the light receiving section to have a light receiving area within which to receive reflection of light from the light emitting section which light receiving area is wider in the perpendicular direction than in the movement direction. Thus, as compared to a reflective sensor including an optical system arranged to, in not only the movement direction but also the perpendicular direction, collect light so that the positional difference is smaller between the regularly reflected light receiving area and the diffuse-reflected light receiving area, the reflective sensor of the present invention has high robustness against a change in the distance between a detection target object and the reflective sensor.

Light may be collimated, instead of collected, for a smaller positional difference between the regularly reflected light receiving area and the diffuse-reflected light receiving area along the direction in which a detection target object is moving. Collecting light, however, has an advantage over collimating light in that the reflective sensor has higher robustness against a change in the angle of the detection target object.

The reflective sensor of the present invention may further be arranged such that the at least one lens section includes (i) a single lens section disposed on either an outward portion of the optical path or a return portion of the optical path or (ii) two lens sections a first one of which is disposed on the outward portion of the optical path and a second one of which is disposed on the return portion of the optical path; and the optical system satisfies $0 \le a \cdot f/(a-f) - d$, where: f represents a focal distance of the at least one lens section along the movement direction; d represents a distance between a center of the at least one lens section and the detection target object; and a represents a distance between the center of the at least one lens section and either the light emitting section or the light receiving section.

The expression $a \cdot f/(a-f) - d$ in the above formula corresponds to the amount of mispositioning along the movement direction between a detection target object and the position at which an image is formed by a lens section. The above formula shows that the amount of the above mispositioning is 0 or greater. This indicates that the above optical system has a wide range of light collecting performance in the movement direction which range covers from (i) collecting light completely for formation of an image on a detection target object to (ii) collecting light incompletely by condensing light further than collimating light for formation of an image at a position beyond the detection target object.

The reflective sensor of the present invention may further be arranged such that the at least one lens section has a curvature along the movement direction which curvature differs from a curvature of the at least one lens section along the perpendicular direction.

Simply using a lens section whose curvature along the movement direction is different from a curvature thereof along the perpendicular direction can easily provide the optical system described above.

The reflective sensor of the present invention may further be arranged such that the optical system satisfies $0 < a \cdot f'/(a-f') - d$ or $a \cdot f'/(a-f') - d = \infty$ and $a \cdot f/(a-f) - d < a \cdot f'/(a-f') - d$, where f' represents a focal distance of the at least one lens section along the perpendicular direction.

As described above, the expression $a \cdot f/(a-f) - d$ corresponds to the amount of mispositioning along the movement direction between a detection target object and the position at which an image is formed by a lens section, and the expression $a \cdot f'/(a-f') - d$ corresponds to the amount of mispositioning along the perpendicular direction between a detection target object and the position at which an image is formed by a lens section. The equation $a \cdot f'/(a-f') - d = \infty$ indicates a lens section that does not collect light but collimates light in the perpendicular direction. Satisfying the above equation reliably allows the light receiving section to have a light receiving area that is wider in the perpendicular direction than in the movement direction.

The reflective sensor of the present invention may preferably further be arranged such that the at least one lens section includes two lens sections a first one of which is disposed on the outward portion of the optical path and a second one of which is disposed on the return portion of the optical path.

Including two lens sections respectively on an outward portion and return portion of the optical path allows a light receiving section to have, for light from a light emitting section, a regularly reflected light receiving area and a diffuse-reflected light receiving area that coincide with each other more accurately. This allows the reflective sensor to have further improved accuracy in position detection.

An image forming apparatus of the present invention includes a belt for carrying an image of a color material; and the reflective sensor as a sensor for detecting both a density of the color material and mispositioning of the color material, the reflective sensor serving to detect the belt as the detection target object.

As described above, the reflective sensor of the present invention has not only accuracy in detecting the position of a detection target object, but also high robustness against at least (i) a change in the distance between the detection target object and the reflective sensor and (ii) a change in the angle of the detection target object with respect to the direction in which the detection target object is moving. Thus, an image forming apparatus including such a reflective sensor is capable of accurately measuring the density and mispositioning of a color material with use of the single sensor.

The present invention is not limited to the description of the embodiments above, but may be altered by a skilled person within the scope of the claims. An embodiment based on a proper combination of technical means disclosed in different embodiments is encompassed in the technical scope of the present invention.

INDUSTRIAL APPLICABILITY

The present invention can be used as a sensor that detects both toner density and mispositioning, and is mounted on an image forming apparatus such as, for example, a copying machine, a printer, and a facsimile machine or the like.

REFERENCE SIGNS LIST

1 Reflective sensor
2 Light emitting element (light emitting section)
3 Light receiving element, first light receiving element (light receiving section)
4 Light receiving element, second light receiving element
20 Detection target object
21 Light emitting section
22 Light receiving section
25, 30, 31, 35 to 37 Lens
27-1 to 27-9 Optical system
51 Image forming apparatus
56 Transfer belt (detection target object)
57 Optical writing device
58 Photoreceptor drum
59 Fixing section
63 Image creating unit
80 Toner patch (detection target object)
P Toner patch (detection target object)
S1 Regularly reflected light receiving area
S2 Diffuse-reflected light receiving area
S3 Irradiation area
F Focal distance

The invention claimed is:

1. A reflective sensor, comprising:
a light emitting section for emitting light toward a detection target object moving in a single direction; and
a light receiving section for receiving regular and diffuse reflection of the light,
the reflective sensor further comprising:
an optical system including at least one lens section each including at least one lens which at least one lens section is disposed on an optical path of light that (i) is emitted by the light emitting section, (ii) travels to the detection target object, (iii) is reflected by the detection target object, and (iv) reaches the light receiving section, the optical system being arranged to, in a movement direction in which the detection target object is moving, collect light so that a regularly reflected light receiving area differs in position from a diffuse-reflected light receiving area by an amount within a predetermined range, the regularly reflected light receiving area being an area present between (i) the detection target object and (ii) the light emitting section and the light receiving section within which area the light emitted by the light emitting section is regularly reflected by the detection target object and is then received by the light receiving section, the diffuse-reflected light receiving area being an area present between (i) the detection target object and (ii) the light emitting section and the light receiving section within which area the light emitted by the light emitting section is diffuse-reflected by the detection target object and is then received by the light receiving section, the optical system being further arranged to, in a perpendicular direction that is perpendicular to the movement direction, refract light so that a light receiving area, which covers the regularly reflected light receiving area and the diffuse-reflected light receiving area, is wider in the perpendicular direction than in the movement direction, the at least one lens section includes (i) a single lens section disposed on either an outward portion of the optical path or a return portion of the optical path or (ii) two lens sections a first one of which is disposed on the outward portion of the optical path and a second one of which is disposed on the return portion of the optical path; and the optical system satisfies $0 < a \cdot f'/(a-f') - d$ where:
f' represents a focal distance of the at least one lens section along the perpendicular direction;
d represents a distance between a center of the at least one lens section and the detection target object; and
a represents a distance between the center of the at least one lens section and either the light emitting section or the light receiving section.

2. The reflective sensor as set forth in claim 1, wherein the at least one lens section has a curvature along the movement direction which curvature differs from a curvature of the at least one lens section along the perpendicular direction.

3. The reflective sensor as set forth in claim 2, wherein the optical system satisfies $0 < a \cdot f/(a-f) - d$ or $a \cdot f/(a-f) - d = \infty$ and $a \cdot f/(a-f) - d < a \cdot f'/(a-f') - d$, where f represents a focal distance of the at least one lens section along the movement direction.

4. The reflective sensor as set forth in claim 3, wherein the at least one lens section includes two lens sections a first one of which is disposed on the outward portion of the optical path and a second one of which is disposed on the return portion of the optical path.

5. An image forming apparatus, comprising:
a belt for carrying an image of a color material; and
as a sensor for detecting both a density of the color material and mispositioning of the color material, a reflective sensor as set forth in claim 2,
the reflective sensor serving to detect the belt as the detection target object.

6. An image forming apparatus, comprising:
a belt for carrying an image of a color material; and
as a sensor for detecting both a density of the color material and mispositioning of the color material, a reflective sensor as set forth in claim 3,
the reflective sensor serving to detect the belt as the detection target object.

7. An image forming apparatus, comprising:
a belt for carrying an image of a color material; and
as a sensor for detecting both a density of the color material and mispositioning of the color material, a reflective sensor as set forth in claim 4,
the reflective sensor serving to detect the belt as the detection target object.

8. An image forming apparatus, comprising:
a belt for carrying an image of a color material; and
as a sensor for detecting both a density of the color material and mispositioning of the color material, a reflective sensor as set forth in claim 1,
the reflective sensor serving to detect the belt as the detection target object.

9. A reflective sensor, comprising:
a light emitting section for emitting light toward a detection target object moving in a single direction; and
a light receiving section for receiving regular and diffuse reflection of the light,
the reflective sensor further comprising:
an optical system including at least one lens section each including at least one lens which at least one lens section is disposed on an optical path of light that (i) is emitted by the light emitting section, (ii) travels to the detection target object, (iii) is reflected by the detection target object, and (iv) reaches the light receiving section,
the optical system being arranged to, in a movement direction in which the detection target object is moving, collect light so that a regularly reflected light receiving area differs in position from a diffuse-reflected light receiving area by an amount within a predetermined range,
the regularly reflected light receiving area being an area present between (i) the detection target object and (ii) the light emitting section and the light receiving section within which area the light emitted by the light emitting section is regularly reflected by the detection target object and is then received by the light receiving section,
the diffuse-reflected light receiving area being an area present between (i) the detection target object and (ii) the light emitting section and the light receiving section within which area the light emitted by the light emitting section is diffuse-reflected by the detection target object and is then received by the light receiving section,
the optical system being further arranged to, in a perpendicular direction that is perpendicular to the movement direction, refract light so that a light receiving area, which covers the regularly reflected light receiving area and the diffuse-reflected light receiving area, is wider in the perpendicular direction than in the movement direction,
the at least one lens section having a curvature along the movement direction which curvature differs from a curvature of the at least one lens section along the perpendicular direction,
wherein the at least one lens section includes (i) a single lens section disposed on either an outward portion of the optical path or a return portion of the optical path or (ii) two lens sections a first one of which is disposed on the outward portion of the optical path and a second one of which is disposed on the return portion of the optical path, and
the optical system satisfies $$0 < a \cdot f'/(a-f') - d,$$

where:
f' represents a focal distance of the at least one lens section along the perpendicular direction;
d represents a distance between a center of the at least one lens section and the detection target object; and
a represents a distance between the center of the at least one lens section and either the light emitting section or the light receiving section,
wherein the optical system satisfies $$0 < a \cdot f/(a-f) - d \text{ or } a \cdot f/(a-f) - d = \infty \text{ and}$$

$$a \cdot f/(a-f) - d < a \cdot f'/(a-f') - d,$$

where f represents a focal distance of the at least one lens section along the movement direction.

10. The reflective sensor as set forth in claim 9, wherein the at least one lens section includes two lens sections a first one of which is disposed on the outward portion of the optical path and a second one of which is disposed on the return portion of the optical path.

11. An image forming apparatus, comprising:
a belt for carrying an image of a color material; and
as a sensor for detecting both a density of the color material and mispositioning of the color material, a reflective sensor as set forth in claim 9,
the reflective sensor serving to detect the belt as the detection target object.

12. An image forming apparatus, comprising:
a belt for carrying an image of a color material; and
as a sensor for detecting both a density of the color material and mispositioning of the color material, a reflective sensor as set forth in claim 10,
the reflective sensor serving to detect the belt as the detection target object.

* * * * *